US009763921B2

(12) United States Patent
Dow et al.

(10) Patent No.: US 9,763,921 B2
(45) Date of Patent: Sep. 19, 2017

(54) DOSING REGIMENS OF CELGOSIVIR FOR THE TREATMENT OF DENGUE

(71) Applicants: 60 Degrees Pharmaceuticals, LLC, Washington, DC (US); National University of Singapore, Singapore (SG); Singapore Health Services PTE Ltd., Singapore (SG)

(72) Inventors: Geoffrey S. Dow, Washington, DC (US); Subhash Vasudevan, Singapore (SG); Mark Reid, Toowong (AU); Glynn Morrish, Toowong (AU); Cynthia Sung, Singapore (SG); Abhay Rathore, Singapore (SG); Satoru Watanabe, Singapore (SG); Eng Eong Ooi, Singapore (SG); Jenny Low, Singapore (SG)

(73) Assignees: 60 Degrees Pharmaceuticals LLC, Washington, DC (US); Singapore Health Services PTE LTD, Singapore (SG); National University Of Singapore, Singapore (SG)

( * ) Notice: Subject to any disclaimer, the term of this patent is extended or adjusted under 35 U.S.C. 154(b) by 0 days.

(21) Appl. No.: 14/772,873

(22) PCT Filed: Mar. 14, 2014

(86) PCT No.: PCT/US2014/028076

§ 371 (c)(1),
(2) Date: Sep. 4, 2015

(87) PCT Pub. No.: WO2014/143907

PCT Pub. Date: Sep. 18, 2014

(65) Prior Publication Data

US 2016/0030403 A1 Feb. 4, 2016

Related U.S. Application Data

(60) Provisional application No. 61/798,100, filed on Mar. 15, 2013, provisional application No. 61/911,795, filed on Dec. 4, 2013.

(51) Int. Cl.
*A61K 31/437* (2006.01)

(52) U.S. Cl.
CPC .................................. *A61K 31/437* (2013.01)

(58) Field of Classification Search
CPC .................................................... A61K 31/437
See application file for complete search history.

(56) References Cited

U.S. PATENT DOCUMENTS

| | | | |
|---|---|---|---|
| 2004/0147549 | A1 | 7/2004 | Tyms et al. |
| 2009/0117083 | A1 | 5/2009 | Nash et al. |

FOREIGN PATENT DOCUMENTS

| | | |
|---|---|---|
| WO | WO 01/54692 | 8/2001 |
| WO | WO 02/089780 | 11/2002 |

OTHER PUBLICATIONS

Rathore et al. Antiviral Research, 2011, vol. 92, pp. 453-460.*
Chateriji et al. Am. J. Trop. Med. Hyg., 2011, vol. 84, No. 2, pp. 224-228.*
International Search Report mailed on Jul. 29, 2014, in corresponding PCT Application No. PCT/US2014/028076.
Low et al., *Celgosivir as a Treatment Against Dengue*, clinicaltrials.gov Identifier: NCT01619969 (Oct. 19, 2012).
PubChem Compound Summary for : CID 60734, Celgosivir, https://pubchem.ncbi.nlm.nih.gov/summary/summary.cgi?cid=60734> (Jun. 26, 2014).
Watanabe et al., *Dose- and schedule-dependent protective efficacy of celgosivir in a lethal mouse model for dengue virus infection informs dosing regimen for a proof of concept clinical trial*, 96 Antiviral Research 32-35 (2012).
Search Report and Written Opinion issued on Oct. 26, 2016, in corresponding Singapore Patent Application No. 11201507254V.

* cited by examiner

*Primary Examiner* — James D Anderson
(74) *Attorney, Agent, or Firm* — Buchanan Ingersoll & Rooney PC

(57) ABSTRACT

Methods of treating a dengue virus (DENV) infection in a human subject, comprising administering to the human subject a compound of Formula (I), or pharmaceutical composition comprising a compound of Formula (I): A compound of Formula (I) can be administered within onset of fever to 72 hours of fever onset due to dengue infection and then every 6 to 12 hours until there is an improvement in the infection or between from about 1 day to about 10 days. The methods of the invention can be used to treat primary and secondary DENV1-4 viral infections.

(I)

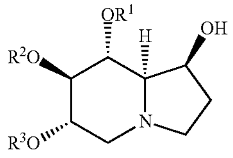

66 Claims, 10 Drawing Sheets

A.

B.

DOSING REGIMENS OF CELGOSIVIR FOR THE TREATMENT OF DENGUE

CROSS-REFERENCE TO RELATED APPLICATIONS

This application is a U.S. National Phase application pursuant to 35 U.S.C. 371 of International Patent Application No. PCT/US2014/028076, filed on Mar. 14, 2014, and published as WO 2014/143907 on Sep. 18, 2014, which claims the benefit of U.S. Provisional Patent Application No. 61/798,100, filed on Mar. 15, 2013, and U.S. Provisional Patent Application No. 61/911,795, filed on Dec. 4, 2013, the entireties of which are incorporated herein by reference for all purposes.

BACKGROUND OF THE INVENTION

Globally, dengue infections result in more than 20,000 deaths, nearly 500,000 hospitalized cases and anywhere between 50-100 million human infections annually. (1) Dengue infection is caused by one of four immunologically distinct serotypes of the dengue virus (DENV 1-4). The virus is spread by the urban breeding mosquito *Aedes aegypti*. Usually, infection with any one of the four DENV serotypes leads to mild, self-limiting dengue fever with lifelong immunity to the specific serotype of infection. Epidemiological evidence also indicates that 90% of the severe and potentially fatal dengue diseases, dengue hemorrhagic fever (DHF) or dengue shock syndrome (DSS) occur during secondary heterotypic infections where the protective antibody from a prior infection takes on a pathogenic role, so-called Antibody Dependent Enhancement (ADE). (2, 3) The antibody response triggers a systemic inflammatory reaction resulting in vascular leakage.

Currently, there is no approved preventive vaccine or antiviral treatment for dengue disease. The World Health Organization has listed dengue fever as an emerging and uncontrolled disease. (4) Hence, there is an urgent medical need for the development of a potent dengue antiviral that is safe for use in humans.

SUMMARY OF THE INVENTION

The present invention pertains to methods of treating a dengue virus (DENV) infection in a human subject. In one aspect, the method comprises administering to the human subject an initial (loading) dose of about 100 to 600 mg of a compound of Formula (I), or a pharmaceutical composition comprising a compound of Formula (I), within from about onset of fever to about 72 hours of fever onset due to dengue infection, followed by administration of one or more subsequent doses of about 25 to about 300 mg of a compound of Formula (I), or a pharmaceutical composition comprising a compound of Formula (I).

In one embodiment, the subsequent doses are administered at intervals of from about 6 to about 12 hours. In other embodiments, the subsequent doses are administered about every 6 hours, about every 8 hours, about every 12 hours, or about every 24 hours.

In certain embodiments, the subsequent doses are administered for about 1-10 days. In other embodiments, the subsequent doses are administered for about 1-5 days, 1-4 days, 1-3 days, 2-3 days, or 1-2 days. In further embodiments, the subsequent doses are administered until there is an improvement in the infection or its symptoms.

In the various embodiments, the human subject can be an adult or a child.

The compound of Formula (I) is represented by the following structure:

(I)

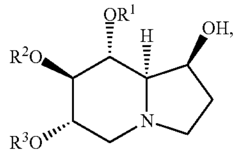

or a pharmaceutically acceptable salt thereof;

wherein $R^1$, $R^2$, and $R^3$ are independently H, $(C_1-C_{14})$ acyl, $(C_1-C_{14})$ alkenylacyl, $(C_3-C_8)$ cycloalkylacyl, $(C_1-C_{14})$ haloalkylacyl $(C_1-C_8)$ alkoxyacyl, or $(C_6-C_{10})$ arylacyl.

In certain embodiments, the compound of Formula (I) is specifically the compound of Formula (II), below, or a pharmaceutically acceptable salt thereof:

(II)

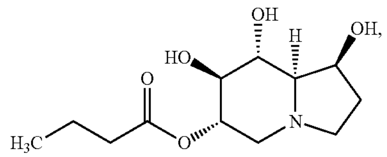

In preferred embodiments, the compound of Formula (I) is prodrug of castanospermine, a natural product derived from the seeds of *Castanospermum australe*. Once administered compounds of Formula (I) are rapidly converted to castanospermine. Compounds of Formula (I) (e.g., celgosivir) are more rapidly and efficiently absorbed than castanospermine. Compounds of Formula (I) are also more readily absorbed into cells. As a result, compounds of Formula (I) may have higher 50% effective concentration (EC50) values and in vivo efficacy than castanospermine against the dengue (DENV) virus.

In certain embodiments, the initial dose is the same as the subsequent doses, while in other embodiments the initial dose differs from the subsequent doses. In particular embodiments, the initial dose is higher than the subsequent doses.

In certain embodiments, for an adult subject, the initial dose of a compound of Formula (I) can be between about 100 to about 600 mg. In other embodiments, the initial dose of a compound of Formula (I) in an adult subject can be about 150-600 mg, about 200-500 mg, or about 250-400 mg. In further embodiments, the initial dose of a compound of Formula (I) in an adult subject can be about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, or about 600 mg. In a further embodiment, the initial dose of a compound of Formula (I) in an adult subject is between about 550 to about 600 mg. In another embodiment, the initial dose of a compound of Formula (I) in an adult subject is between about 500 to about 550 mg. In yet another embodiment, the initial dose of a compound of Formula (I) in an adult subject is between about 450 to about 500 mg. In further embodiment, the initial dose of a compound of Formula (I) in an adult subject is between about 400 to about 450 mg. In another embodiment, the initial dose of a compound of Formula (I) in an adult subject is between about 350 to about 400 mg. In further embodiment, the initial dose of compound of Formula (I) in an adult subject is between about 300 to about 350 mg. In yet another embodiment, the initial dose of a compound of Formula (I) in an adult subject is between about 250 to about 300 mg. In further embodiment, the initial dose of compound of Formula (I) in an adult subject is between about 200 to about 250 mg. In another embodiment, the initial dose of a compound of Formula (I) in an adult subject is between about 150 to about 200 mg. In another embodiment, the initial dose of compound of Formula (I) in an adult subject is between about 100 to about 150 mg.

The subsequent doses of a compound of Formula (I) in an adult subject can be between about 100 to about 300 mg. In one embodiment, the subsequent dose of a compound of Formula (I) in an adult subject is between about 250 to about 300 mg. In another embodiment the subsequent dose of a compound of Formula (I) in an adult subject is between about 200 to about 250 mg. In yet another embodiment, the subsequent dose of a compound of Formula (I) in an adult subject is between about 150 to about 200 mg. In further embodiment, the subsequent dose of a compound of Formula (I) in an adult subject is between about 100 to about 200 mg. In an additional embodiment, the subsequent dose of a compound of Formula (I) in an adult subject is between about 125 to about 175 mg. In yet another embodiment, the subsequent dose of a compound of Formula (I) in an adult subject is about 150 mg.

For a child subject, the initial dose of a compound of Formula (I) in a child subject can be between about 25 to about 450 mg. In one embodiment, the initial dose of a compound of Formula (I) in a child subject is between about 25 to about 50 mg. In another embodiment, the initial dose of a compound of Formula (I) in a child subject is between about 50 to about 75 mg. In yet another embodiment, the initial dose of a compound of Formula (I) in a child subject is between about 75 to about 100 mg. In further embodiment, the initial dose of a compound of Formula (I) in a child subject is between about 100 to about 150 mg. In another embodiment, the initial close of a compound of Formula (I) in a child subject is between about 150 to about 200 mg. In yet another embodiment, the initial dose of a compound of Formula (I) in a child subject is between about 200 to about 250 mg. In further embodiment, the initial dose of a compound of Formula (I) in a child subject is between about 250 to about 300 mg. In another embodiment, the initial dose of a compound of Formula (I) in a child subject is between about 300 to about 350 mg. In yet another embodiment, the initial dose of a compound of Formula (I) in a child subject is between about 350 to about 400 mg.

The subsequent doses of a compound of Formula (I) in a child subject can be between about 25 to about 200 mg. In one embodiment, the subsequent dose of a compound of Formula (I) in a child subject is between about 25 to about 50 mg. In another embodiment, the subsequent dose of a compound of Formula (I) in a child subject is between about 50 to about 75 mg. In yet another embodiment, the subsequent dose of a compound of Formula (I) in a child subject is between about 75 to about 100 mg. In further embodiment, the subsequent dose of a compound of Formula (I) in a child subject is between about 100 to about 125 mg. In another embodiment, the subsequent dose of a compound of Formula (I) in a child subject is between about 125 to about 150 mg. In yet another embodiment, the subsequent dose of a compound of Formula (I) in a child subject is between about 150 to about 200 mg.

In one embodiment, the initial close is administered at the time of fever onset due to dengue infection. In another embodiment, the initial dose is administered within 24 hours of fever onset due to dengue infection. In yet another embodiment, the initial dose is administered within 48 hours of fever onset due to dengue infection. In a further another embodiment, the initial dose is administered within 72 hours of fever onset due to dengue infection.

The compounds or pharmaceutical compositions of the present invention can be administered intravenously, orally, rectally or sublingually. In one embodiment, the route of administration is intravenous. In another embodiment, the route of administration is oral. In another embodiment, the route of administration is rectal. In yet another embodiment, the route of administration is sublingual.

The compounds or pharmaceutical compositions of the present invention can be administered as a single or as a divided dose. Preferably, the initial dose is a single dose. In some embodiments, the subsequent doses can be single, divided, or a combination thereof, during the course of therapy depending upon patient and progress of the infection. For the subsequent doses in one embodiment, the human subject is administered a divided dose of from about 25 to about 300 mg of a compound of Formula (I), or a pharmaceutical composition comprising a compound of Formula (I), for between about 1 day to about 10 days. In another embodiment, the human subject is administered a single dose of from about 25 to about 300 mg of a compound of Formula (I), or a pharmaceutical composition comprising a compound of Formula (I), for between about 1 day to about 10 days. In yet another embodiment, the human subject is administered a single dose of from about 25 to about 300 mg of a compound of Formula (I), or a pharmaceutical composition comprising a compound of Formula (I), for between about 1 day to about 2 days. In a further embodiment, the human subject is administered a single dose of from about 25 to about 300 mg of a compound of Formula (I), or a pharmaceutical composition comprising a compound of Formula (I), for between about 2 days to about 5 days. In other versions, the subsequent doses are administered no longer than about 1 day; in yet other versions no longer than about 2 days; in further versions no longer than about 5 days; and other versions no longer than about 10 days.

The invention also relates to methods of treating a dengue virus infection by achieving a steady state Cmin serum or plasma concentration of between about 0.05 and about 2.0 microgram/mL of castanospermine in an adult or child subject. In one embodiment, the steady state Cmin serum or plasma concentration achieved in an adult or child subject is between about 0.08 and about 0.5 microgram/mL of castanospermine. In another embodiment, the steady state Cmin serum or plasma concentration achieved in an adult or child subject is between about 0.05 and about 0.08 microgram/mL of castanospermine. In yet another embodiment, the steady state Cmin serum or plasma concentration achieved in an adult or child subject is between about 0.08 and about 0.11 microgram/mL of castanospermine. In a further embodiment, the steady state Cmin serum or plasma concentration achieved in an adult or child subject is between about 0.11 and about 0.3 microgram/mL of castanospermine. In another embodiment, the steady state Cmin serum or plasma concentration achieved in an adult or child subject is between about 0.3 and about 0.75 microgram/mL of castanospermine. In further embodiment, the steady state Cmin serum or plasma concentration achieved in an adult or child subject is between about 0.75 and about 1.0 microgram/mL of castanospermine. In yet another embodiment, the steady state Cmin serum or plasma concentration achieved in an adult or child subject is between about 1.0 and about 2.0 microgram/mL of castanospermine. In another embodiment, the steady state Cmin serum or plasma concentration achieved in an adult or child subject is between about 1.0 and about 1.5 microgram/mL of castanospermine. In further embodiment, the steady state Cmin serum or plasma concentration achieved in an adult or child subject is between about 1.5 and about 2.0 microgram/mL of castanospermine. In yet another embodiment, the steady state Cmin serum or plasma concentration achieved in an adult or child subject is between about 1.25 and about 1.75 microgram/mL of castanospermine.

In another aspect, the invention relates to methods for treating a dengue viral infection comprising at least one dengue virus selected from DENV1, DENV2, DENV3 and DENV4. In one embodiment, the dengue virus is DENV1. In another embodiment, the dengue virus is DENV2. In yet another embodiment, the dengue virus is DENV3. In further embodiment, the dengue virus is DENV4.

In yet another aspect, the invention relates to methods of treating a dengue viral infection in a human subject who has tested positive for dengue virus. Known methods for diagnosis of dengue viral infection can be used including, but are not limited to, an NS1 (nonstructural protein 1) strip assay or a quantitative Polymerase Chain Reaction (PCR) assay. The selected method should be rapid enough for a diagnosis within from about onset of fever to about 72 hours of fever onset to optimize the therapeutic regimen of the various embodiments of the invention.

The invention also relates to methods of treating a secondary dengue (DENV) viral infection in a human subject, comprising administering to the human subject an initial dose of about 100 to about 600 mg of a compound of Formula (I), or a pharmaceutical composition comprising a compound of Formula (I), within from about onset of fever to about 72 hours of fever onset due to dengue infection and administering to the human subject a dose of about 25 to about 300 mg of a compound of Formula (I), or a pharmaceutical composition comprising a compound of Formula (I), at intervals of from about 6 to about 12 hours until there is an improvement in the infection or between from about 1 day to about 10 days.

In another aspect of the invention, viral load reduction of treated human subjects is at least 50% greater than untreated or placebo-treated human subjects. In one embodiment, the virological log reduction in human subjects treated with a compound of Formula (I) is at least 50% greater than untreated or placebo-treated groups. In another embodiment, the virological log reduction in human subjects treated with a compound of Formula (I) is between about 60 to about 70% greater than untreated or placebo-treated groups. In another embodiment, the virological log reduction in human subjects treated with a compound of Formula (I) is between about 70 to about 80% greater than untreated or placebo-treated groups. In yet another embodiment, the virological log reduction in human subjects treated with a compound of Formula (I) is between about 80 to about 90% greater than untreated or placebo-treated groups.

The invention is also directed to methods of treating a dengue viral infection comprising administering a pharmaceutical composition comprising a compound of Formula (I), Formula (II), or Formula (III) according to any one of the dosing regimens described herein. The disclosed compounds of Formula (I), Formula (II) or Formula (III) can be administered to the subject in conjunction with an acceptable pharmaceutical carrier or diluent as part of a pharmaceutical composition for treatment of a dengue (DENV) infection.

BRIEF DESCRIPTION OF THE DRAWINGS

The foregoing will be apparent from the following more particular description of example embodiments of the invention, as illustrated in the accompanying drawings.

DETAILED DESCRIPTION OF THE INVENTION

Figure 1:
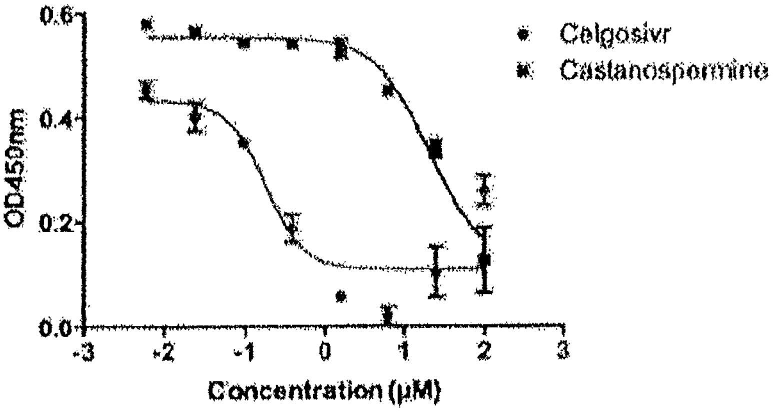
FIG. 1 shows a concentration response curve of celgosivir on DENV2 infection in the Cell-based flaviviral immunodetection assay (CFI) assay; EC50 ranges from 0.2 to 0.7 μM.

A description of example embodiments of the invention follows.

Definitions

All definitions of substituents set forth below are further applicable to the use of the term in conjunction with another substituent. Unless defined otherwise, all technical and scientific terms used herein have the same meaning as commonly understood by one of ordinary skill in the art to which this invention belongs.

"Alkyl" as used alone or as part of a larger moiety as in "arylalkyl" or "aryloxyalkyl" means a saturated aliphatic branched or straight-chain monovalent hydrocarbon radicals, typically C1-C16, preferably C1-C12. For example, "(C1-C6) alkyl" means a radical having from 1-6 carbon atoms in a linear or branched arrangement. "(C1-C6) alkyl" includes methyl, ethyl, propyl, butyl, tert-butyl, pentyl and hexyl.

"Alkylene" means a saturated aliphatic straight-chain divalent hydrocarbon radical. Thus, "($C_1$-$C_6$) alkylene" means a divalent saturated aliphatic radical having from 1-6 carbon atoms in a linear arrangement. "($C_1$-$C_6$) alkylene" includes methylene, ethylene, propylene, butylene, pentylene and hexylene.

"Cycloalkyl" means saturated aliphatic cyclic hydrocarbon ring. Thus, "$C_3$-$C_3$ cycloalkyl" means (3-8 membered) saturated aliphatic cyclic hydrocarbon ring. $C_3$-$C_8$ cycloalkyl includes, but is not limited to cyclopropyl, cyclobutyl, cyclopentyl, cyclohexyl, cycloheptyl, and cyclooctyl. Preferably, cycloalkyl is $C_3$-$C_6$ cycloalkyl.

The term "alkoxy" means —O-alkyl; "arylalkoxy" means an alkoxy group substituted at any carbon by an aryl group; "hydroxyalkyl" means alkyl substituted with hydroxy; "arylalkyl" means alkyl substituted with an aryl group; "alkoxyalkyl" mean alkyl substituted with an alkoxy group; "cycloalkylalkyl" means alkyl substituted with cycloalkyl; "alkylcarbonyl" means —C(O)-A*, wherein A* is alkyl; "alkoxycarbonyl" means —C(O)—OA*, wherein A* is alkyl; and where alkyl is as defined above. Alkoxy is preferably O($C_1$-$C_6$) alkyl and includes methoxy, ethoxy, propoxy, butoxy, pentoxy and hexoxy.

"Cycloalkoxy" means a cycloalkyl-O— group wherein the cycloalkyl is as defined above, Exemplary ($C_3$-$C_7$) cycloalkyloxy groups include cyclopropoxy, cyclobutoxy, cyclopentoxy, cyclohexoxy and cycloheptoxy.

"Halogen" and "halo" are interchangeably used herein and each refers to fluorine, chlorine, bromine, or iodine.

The terms "haloalkyl", "halocycloalkyl" and "haloalkoxy" mean alkyl, cycloalkyl, or alkoxy, as the case may be, substituted with one or more halogen atoms. The term "halogen" or "halo" means F, Cl, Br or I.

"Acyl" refers to R"—C(O)—, where R" is H, alkyl, substituted alkyl, heteroalkyl, substituted heteroalkyl, alkenyl, substituted alkenyl, aryl, alkylaryl, or substituted alkylaryl, and is indicated in the general formula of a particular embodiment as "Ac".

An "alkylene group" is represented by $—[CH_2]_z—$, wherein z is a positive integer, preferably from one to eight, more preferably from one to four.

An "alkenylene group" is an alkylene in which at least a pair of adjacent methylenes are replaced with —CH═CH—.

The term "($C_6$-$C_{10}$) aryl" used alone or as part of a larger moiety as in "arylalkyl", "arylalkoxy", "aryloxy", or "aryloxyalkyl", means carbocyclic aromatic rings. The term "carbocyclic aromatic group" may be used interchangeably with the terms "aryl", "aryl ring" "carbocyclic aromatic ring", "aryl group" and "carbocyclic aromatic group". An aryl group typically has 6-10 ring atoms. A "substituted aryl group" is substituted at any one or more substitutable ring atom. The term "$C_6$-$C_{16}$ aryl" as used herein means a monocyclic, bicyclic or tricyclic carbocyclic ring system containing from 6 to 16 carbon atoms and includes phenyl (Ph), naphthyl, anthracenyl, 1,2-dihydronaphthyl, 1,2,3,4-tetrahydronaphthyl, fluorenyl, indanyl, indenyl and the like. The ($C_6$-$C_{10}$) aryl ($C_1$-$C_6$) alkyl group connects to the rest of the molecule through the ($C_1$-$C_6$) alkyl portion of the ($C_6$-$C_{10}$) aryl ($C_1$-$C_6$) alkyl group.

The term "Alkenyl" as used alone or as part of a larger moiety as in "Alkenylacyl" or "haloalkylacyl" means a straight or branched hydrocarbon radical having a specified number of carbon atoms and includes at least one double bond. An alkenyl group generally has between 2 and 6 carbon atoms. The ($C_6$-$C_{10}$) aryl ($C_2$-$C_6$) alkenyl group connects to the remainder of the molecule through the ($C_2$-$C_6$) alkenyl portion of ($C_6$-$C_{10}$) aryl ($C_2$-$C_6$) alkenyl.

"Alkenylacyl" refers to an acyl group, R"—C(O)—, where R" is an alkenyl or a substituted alkenyl (e.g., $CH_3$—CH═CH—C(O)—).

"Pharmaceutically acceptable carrier" means non-therapeutic components that are of sufficient purity and quality for use in the formulation of a composition of the invention that, when appropriately administered to typically do not produce an adverse reaction, and that are used as a vehicle for a drug substance (e.g., a compound of Formula (I)).

"Intraperitoneal injection," as used herein, refers to the injection of a substance into the peritoneum (body cavity).

"Three times a day dosing", as used herein, refers to three administrations of a pharmaceutical composition per every 24 hour period.

"Four times a day dosing" (QDS), as used herein, refers to four administrations of a pharmaceutical composition per every 24 hour period.

As used herein, "BDI" refers to twice daily. Further, as used herein, "QD" refers to once daily.

As used herein, "Cmin" refers to the minimum concentration that a drug achieves after the drug has been administered and prior to the administration of a second or additional dose. Further, "Cmax", as used herein, refers to the maximum concentration. Similarly, "Tmax", as used herein, refers to the time of maximum concentration. Additionally, "AUC", used herein, is the area under the concentration-time curve. Additionally, "50% effective concentration" (EC50), as used herein, refers to the concentration of an anti-viral that produces 50% of the maximal possible antiviral effect.

As used herein, the term "about" refers to a number that differs from the given number by less than 10%. In other embodiments, the term "about" indicates that the number differs from the given number by less than 9%, 8%, 7%, 6%, 5%, 4%, 3%, 2%, or 1%.

The abbreviation "DENV", as used herein, refers to dengue virus. Further the four serotypes of the dengue virus are used herein as "DENV1", "DENV2", "DENV3" and "DENV4".

"Antibody enhanced" or "Antibody Dependent Enhancement" (ADE), as used herein interchangeably, refers to a DENV infection made more severe due to a prior infection with one of the four DENV serotypes: DENV1, DENV2, DENV3, and DENV4.

As used herein, "dengue hemorrhagic fever" (DHF) and "dengue shock syndrome" (DSS), refers to the severe and potentially fatal dengue diseases that often occur during secondary heterotypic infections.

As used herein, "viral load" refers to the amount of virus in the blood stream of a human subject.

Dosing Regimen

The present invention pertains to methods of treating a dengue virus (DENV) infection in a human subject, comprising administering to the human subject an initial dose of about 100 to about 600 mg of a compound of Formula (I), or a pharmaceutical composition comprising a compound of Formula (I), within from about onset of fever to about 72 hours of fever onset due to dengue infection and administering to the human subject a dose of about 25 to about 300 mg of a compound of Formula (I), or a pharmaceutical composition comprising a compound of Formula (I), at intervals of from about 6 to about 12 hours until there is an improvement in the infection or between from about 1 day to about 10 days.

In one embodiment, the compound of the invention is a compound of Formula (I):

(I)

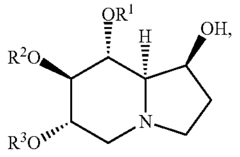

or a pharmaceutically acceptable salt there of;

wherein $R^1$, $R^2$, and $R^3$ are independently H, (C1-C14) acyl, (C1-C14) alkenylacyl, (C3-C8) cycloalkylacyl, (C1-C14) haloalkylacyl (C1-C8) alkoxyacyl, or (C6-C10) arylacyl.

In another embodiment, $R^1$ and $R^2$ are H and $R^3$ is a (C1-C14) acyl. In another embodiment, $R^1$ is $CH_3$—$CH_2CH_2$—C(O)—. In yet another embodiment, $R^2$ is $CH_3$—$CH_2CH_2$—C(O)—. In a further embodiment, $R^3$ is $CH_3$—$CH_2CH_2$—C(O)—. In another embodiment, at least one but not more than two R1, R2, and R3 is a hydrogen.

In yet another embodiment, the compound of the invention is a compound of Formula (II):

(II)

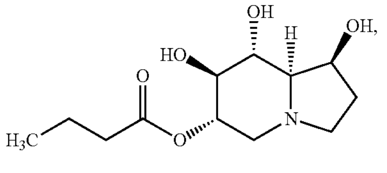

or a pharmaceutically acceptable salt thereof.

The compound of Formula (II), or pharmaceutical composition comprising a compound of Formula (II), can be used in any of the embodiments provided herein for Formula (I).

In further embodiment, the compound of the invention is a compound of Formula (III):

(III)

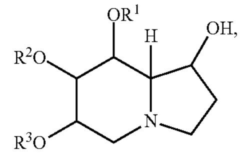

or a pharmaceutically acceptable salt there of;

wherein $R^1$, $R^2$, and $R^3$ are independently H, (C1-C14) acyl, (C1-C14) alkenylacyl, (C3-C8) cycloalkylacyl, (C1-C14) haloalkylacyl (C1-C8) alkoxyacyl, or (C6-C10) arylacyl.

The compound of Formula (III), or pharmaceutical composition comprising a compound of Formula (III), can be used in any of the embodiments provided herein for Formula (I).

The compounds of the invention useful for practicing the methods described herein may possess one or more chiral centers and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilizing methods known to those skilled in the art. In addition, chiral intermediate compounds may be resolved and used to prepare chiral compounds of the invention.

The compounds described herein may exist in one or more tautomeric forms. All tautomers and mixtures thereof are included in the scope of the present invention.

The compounds of the present invention can be administered as the free base or as a pharmaceutically acceptable salt. For example, an acid salt of a compound of the present invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estotate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts. In one embodiment, the compound of Formula (I) is a hydrochloride salt. In another embodiment, the compound of Formula (II) is a hydrochloride salt.

The invention is also directed to methods of the invention using a pharmaceutical composition comprising a compound of Formula (I) or Formula (II). The disclosed compounds of Formula (I) and Formula (II) can be administered to the subject in conjunction with an acceptable pharmaceutical carrier or diluent as part of a pharmaceutical composition for treatment of a dengue (DENV) infection, and according to any of the dosing regimens described herein. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

In one embodiment, the pharmaceutical composition comprises a pharmaceutically acceptable carrier or diluent and a compound Formula (I). In another embodiment, the pharmaceutical composition comprises a pharmaceutically acceptable carrier or diluent and a compound Formula (II).

In preferred embodiments, the compound of Formula (I) is prodrug of castanospermine, a natural product derived from the seeds of *Castanospermum australe*. Once administered compounds of Formula (I) are rapidly converted to castanospermine. Compounds of Formula (I) (e.g., celgosivir) are more rapidly and efficiently absorbed than castanospermine. Compounds of Formula (I) are also more readily absorbed into cells. As a result, compounds of Formula (I) may have higher EC50 values and in vivo efficacy than castanospermine against the dengue (DENV) virus.

Castanospermine has been shown to exert antiviral activity by inhibiting host alpha-glucosidases I and II, enzymes essential for proper folding of dengue-virus encoded glycoproteins such as E and prM. (6,7) Castanospermine targets dengue NS1 protein folding in dengue virus infected cells. Impaired glycosylation of the NS1 protein leads to accumulation of proteins in the endoplasmic reticulum (ER) and drastically inhibits the virus replication. Since the drug target is a host enzyme required for viral maturation, the potential for development of resistance is expected to be lower than a drug directed against a viral enzyme.

The methods of the invention treat a human subject having a dengue viral infection. As used herein "treating" or "treatment" refers to obtaining desired pharmacological and/or physiological effects. The effect can include achieving, partially or substantially one or more of the following results: partially or totally reducing the extent of the disease, disorder or syndrome; ameliorating or improving a clinical symptom or indicator associated with the disease, disorder or syndrome; delaying, inhibiting or decreasing the likelihood of the progression of the disease, disorder or syndrome.

The initial dose of a compound of Formula (I), or a pharmaceutical composition comprising a compound of Formula (I), can be administered at any time within from about the onset of fever to about 72 hours after fever onset due to dengue infection. In one embodiment, the initial dose is administered at the time of fever onset. In another embodiment, the initial dose is administered within from about 24 hours of fever onset. In yet another embodiment, the initial dose is administered within from about 48 hours of fever onset. In a further embodiment, the initial dose is administered within from about 72 hours of fever onset. Subsequent doses can be the same amount or vary to achieve steady state Cmin or plasma concentrations in the subject.

The human subject may be an adult or a child. As used herein, a "child" refers to a human subject who is between the ages of 1 day to 17 years of age. The term "adult" refers to a human subject who is 18 years of age or older. Further, the plurality of human subjects may include adults or children. In some embodiments, the plurality of human subjects may include only adults. In another embodiment, the plurality of human subjects may include only children. In yet another embodiment, the plurality of human subjects may include both adults and children.

In another aspect, the present invention relates to a method of treating a dengue invention in an adult subject comprising administering to the adult subject an initial dose of about 100 to about 600 mg of a compound of Formula (I), or a pharmaceutical composition comprising a compound of Formula (I), within from about onset of fever to about 72 hours of fever onset due to dengue infection and administering to the adult subject a dose of about 25 to about 300 mg of a compound of Formula (I), or a pharmaceutical composition comprising a compound of Formula (I), at intervals of from about 6 to about 12 hours until there is an improvement in the infection or between about 1 day to about 10 days.

Example embodiments of initial and subsequent doses in an adult are shown in Table 1:

TABLE 1

Dosing Regimen for an Adult

| Embodiment | Initial dose (mg)[1] | Subsequent dose (mg)[2,3] |
|---|---|---|
| 1 | 100 | 100 |
| 2 | 150 | 100 |
| 3 | 200 | 100 |
| 4 | 250 | 100 |
| 5 | 300 | 100 |
| 6 | 350 | 100 |
| 7 | 400 | 100 |
| 8 | 450 | 100 |
| 9 | 500 | 100 |
| 10 | 550 | 100 |
| 11 | 600 | 100 |
| 12 | 100 | 150 |
| 13 | 150 | 150 |
| 14 | 200 | 150 |
| 15 | 250 | 150 |
| 16 | 300 | 150 |
| 17 | 350 | 150 |
| 18 | 400 | 150 |
| 19 | 450 | 150 |
| 20 | 500 | 150 |
| 21 | 550 | 150 |
| 22 | 600 | 150 |
| 23 | 600 | 175 |
| 24 | 100 | 200 |
| 25 | 150 | 200 |
| 26 | 200 | 200 |
| 27 | 250 | 200 |
| 28 | 300 | 200 |
| 29 | 350 | 200 |
| 30 | 400 | 200 |
| 31 | 450 | 200 |
| 32 | 500 | 200 |
| 33 | 550 | 200 |
| 34 | 600 | 200 |
| 35 | 100 | 250 |
| 36 | 150 | 250 |
| 37 | 200 | 250 |
| 38 | 250 | 250 |
| 39 | 300 | 250 |
| 40 | 350 | 250 |
| 41 | 400 | 250 |

TABLE 1-continued

| Dosing Regimen for an Adult | | |
|---|---|---|
| Embodiment | Initial dose (mg)[1] | Subsequent dose (mg)[2,3] |
| 42 | 450 | 250 |
| 43 | 500 | 250 |
| 44 | 500 | 250 |
| 45 | 550 | 250 |
| 46 | 600 | 250 |
| 47 | 100 | 300 |
| 48 | 150 | 300 |
| 49 | 200 | 300 |
| 50 | 250 | 300 |
| 51 | 300 | 300 |
| 52 | 350 | 300 |
| 53 | 400 | 300 |
| 54 | 450 | 300 |
| 55 | 450 | 300 |
| 56 | 500 | 300 |
| 57 | 500 | 300 |
| 58 | 550 | 300 |
| 59 | 600 | 300 |

[1]Initial dosing within about onset of fever to about 72 hours.
[2]Subsequent dosing periodically from about 6 to about 12 hours.
[3]Length of subsequent dosing, a) until infection improves, b) between about 1 day to 2 days, c) between about 2 to 3 days, d) between about 3 to 4 days, d) between about 4 to 5 days, e) between about 5 to 7 day, or f) between about 7 to 10 days.

In another aspect, the present invention relates to methods of treating a dengue invention in an child subject comprising administering to the child subject an initial dose of about 100 to about 600 mg of a compound of Formula (I), or a pharmaceutical composition comprising a compound of Formula (I), within from about onset of fever to about 72 hours of fever onset due to dengue infection and administering to the child subject a dose of about 25 to about 300 mg of a compound of Formula (I), or a pharmaceutical composition comprising a compound of Formula (I), at intervals of from about 6 to about 12 hours until there is an improvement in the infection or between from about 1 day to about 10 days.

Example embodiments of initial and subsequent doses combinations in a child are shown in Table 2:

TABLE 2

| Dosing Regimen for a Child | | |
|---|---|---|
| Embodiment | Initial dose (mg)[4] | Subsequent dose (mg)[5,6] |
| 1 | 25 | 25 |
| 2 | 50 | 25 |
| 3 | 75 | 25 |
| 4 | 100 | 25 |
| 5 | 150 | 25 |
| 6 | 200 | 25 |
| 7 | 250 | 25 |
| 8 | 300 | 25 |
| 9 | 25 | 50 |
| 10 | 50 | 50 |
| 11 | 75 | 50 |
| 12 | 100 | 50 |
| 13 | 150 | 50 |
| 14 | 200 | 50 |
| 15 | 250 | 50 |
| 16 | 300 | 50 |
| 17 | 25 | 75 |
| 18 | 50 | 75 |
| 19 | 75 | 75 |
| 20 | 100 | 75 |
| 21 | 150 | 75 |
| 22 | 200 | 75 |
| 23 | 250 | 75 |

TABLE 2-continued

| Dosing Regimen for a Child | | |
|---|---|---|
| Embodiment | Initial dose (mg)[4] | Subsequent dose (mg)[5,6] |
| 24 | 300 | 75 |
| 25 | 25 | 100 |
| 26 | 50 | 100 |
| 27 | 75 | 100 |
| 28 | 100 | 100 |
| 29 | 150 | 100 |
| 30 | 200 | 100 |
| 31 | 250 | 100 |
| 32 | 300 | 100 |
| 33 | 25 | 150 |
| 34 | 50 | 150 |
| 35 | 75 | 150 |
| 36 | 100 | 150 |
| 37 | 150 | 150 |
| 38 | 200 | 150 |
| 39 | 250 | 150 |
| 40 | 300 | 150 |
| 41 | 25 | 200 |
| 42 | 50 | 200 |
| 43 | 75 | 200 |
| 44 | 100 | 200 |
| 45 | 150 | 200 |
| 46 | 200 | 200 |
| 47 | 250 | 200 |
| 48 | 300 | 200 |

[4]Initial dosing within about onset of fever to about 72 hours.
[5]Subsequent dosing periodically from about 6 to about 12 hours.
[6]Length of subsequent dosing, a) until infection improves, b) between about 1 day to 2 days, c) between about 2 to 3 days, d) between about 3 to 4 days, d) between about 4 to 5 days, e) between about 5 to 7 day, or f) between about 7 to 10 days.

The human subject can be administered a compound of the present invention for a period of about between about 1 day to about 10 days. In one embodiment, the subsequent dose of a compound of Formula (I), or a pharmaceutical composition comprising a compound of Formula (I), is administered for about 1 day to about 2 days. In further embodiment, the subsequent dose of a compound of Formula (I), or a pharmaceutical composition comprising a compound of Formula (I), is administered for about 2 to about 3 days. In another embodiment, the subsequent dose of a compound of Formula (I), or a pharmaceutical composition comprising a compound of Formula (I), is administered for about 3 to about 5 days. In yet another embodiment, the subsequent dose of a compound of Formula (I), or a pharmaceutical composition comprising a compound of Formula (I), is administered for about 5 to about 7 days. In another embodiment, the subsequent dose of a compound of Formula (I), or a pharmaceutical composition comprising a compound of Formula (I), is administered for about 7 to about 10 days.

The present invention pertains to methods of treating a dengue virus (DENV) infection in a human subject, comprising administering to the human subject an initial dose of about 100 to about 600 mg of a compound of Formula (I), or a pharmaceutical composition comprising a compound of Formula (I), within from about onset of fever to about 72 hours of fever onset due to dengue infection; and administering to the human subject a dose of about 25 to about 300 mg of a compound of Formula (I), or a pharmaceutical composition comprising a compound of Formula (I), at intervals of from about 6 to about 12 hours until there is an improvement in the infection or between from about 1 day to about 10 days, wherein $R^1$, $R^2$, and $R^3$ are independently H, (C1-C14) acyl, (C1-C14) alkenylacyl, (C3-C8) cycloalkylacyl, (C1-C14) haloalkylacyl (C1-C8) alkoxyacyl, or (C6-C10) arylacyl.

The invention is also directed to methods of treating a secondary dengue infection in a human subject, comprising administering to the human subject an initial dose of about 100 to about 600 mg of a compound of Formula (I), or a pharmaceutical composition comprising a compound of Formula (I), within from about onset of fever to about 72 hours of fever onset due to dengue infection; and administering to the human subject a dose of about 25 to about 300 mg of a compound of Formula (I), or a pharmaceutical composition comprising a compound of Formula (I), at intervals of from about 6 to about 12 hours until there is an improvement in the infection or between from about 1 day to about 10 days, wherein $R^1$, $R^2$, and $R^3$ are independently H, (C1-C14) acyl, (C1-C14) alkenylacyl, (C3-C8) cycloalkylacyl, (C1-C14) haloalkylacyl (C1-C8) alkoxyacyl, or (C6-C10) arylacyl.

In one embodiment of the invention, the compound of Formula (I), is a compound of Formula (II) or a pharmaceutically acceptable salt thereof.

The invention also relates to methods of treating a dengue virus (DENV) infection in a human subject, comprising administering to the human subject an initial dose of about 100 to about 600 mg of a compound of Formula (II), or a pharmaceutical composition comprising a compound of Formula (II), within from about onset of fever to about 72 hours of fever onset due to dengue infection; and administering to the human subject a dose of about 25 to about 300 mg of a compound of Formula (II), or a pharmaceutical composition comprising a compound of Formula (II), at intervals of from about 6 to about 12 hours until there is an improvement in the infection or between from about 1 day to about 10 days.

In another aspect, the invention relates to methods of treating a dengue virus (DENV) infection in a human subject, comprising administering orally to the human subject an initial dose of about 100 to about 600 mg of a compound of Formula (I), or a pharmaceutical composition comprising a compound of Formula (I), within from about onset of fever to about 72 hours of fever onset due to dengue infection; and administering orally to the human subject a dose of about 25 to about 300 mg of a compound of Formula (I), or a pharmaceutical composition comprising a compound of Formula (I), at intervals of from about 6 to about 12 hours until there is an improvement in the infection or between from about 1 day to about 10 days, wherein $R^1$, $R^2$, and $R^3$ are independently H, (C1-C14) acyl, (C1-C14) alkenylacyl, (C3-C8) cycloalkylacyl, (C1-C14) haloalkylacyl (C1-C8) alkoxyacyl, or (C6-C10) arylacyl.

In yet another aspect, the invention pertains to methods of treating a dengue virus (DENV) infection in a human subject, comprising administering to the human subject an initial dose of about 100 to about 600 mg of a compound of Formula (III), or a pharmaceutical composition comprising a compound of Formula (III), within from about onset of fever to about 72 hours of fever onset due to dengue infection; and administering to the human subject a dose of about 25 to about 300 mg of a compound of Formula (III), or a pharmaceutical composition comprising a compound of Formula (III), at intervals of from about 6 to about 12 hours until there is an improvement in the infection or between from about 1 day to about 10 days; wherein $R^1$, $R^2$, and $R^3$ are independently H, (C1-C14) acyl, (C1-C14) alkenylacyl, (C3-C8) cycloalkylacyl, (C1-C14) haloalkylacyl (C1-C8) alkoxyacyl, or (C6-C10) arylacyl.

In certain embodiments of the invention, the human subject is an adult or a child. In further embodiments of the invention, the plurality of human subjects may include adults or children. In some embodiments, the plurality of human subjects may include only adults. In another embodiment, the plurality of human subjects may include only children. In yet another embodiment, the plurality of human subjects may include both adults and children.

In certain embodiments of the invention, each of the plurality of human subjects may be given a different dose. In another embodiment, each of the plurality of human subjects may be given the same dose. In further embodiment, each of the plurality of human subjects may be given a variety of doses. In yet another embodiment, some of the plurality of the human subjects may be given the same dose and some of the plurality of the human subjects may be given a different dose.

In another embodiment, compound of Formula (I), the compound of Formula (II), or the compound of Formula (III) is converted to castanospermine after administration to a human subject.

In yet another embodiment, a steady state Cmin serum or plasma concentration of between about 0.05 and about 2.0 microgram/mL of castanospermine in an adult or child human subject is attained.

In one embodiment of the invention, dengue viral infection comprises at least one dengue virus selected from DENV1, DENV2, DENV3 and DENV4. In another embodiment, the dengue viral infection is secondary dengue infection. In yet another embodiment of the invention, the human subject to be treated is positive for a dengue infection using a NS1 strip assay or quantitative PCR. In further embodiment of the invention, the virological log reduction in treated human subjects is at least 50% greater than untreated or placebo-treated groups. In yet another embodiment, administering the compound, or the pharmaceutical composition, achieves a steady state Cmin serum or plasma concentration of between about 0.05 and about 2.0 microgram/mL of castanospermine. In another embodiment of the invention, the compound, or the pharmaceutical composition, is administered intravenously, orally, rectally or sublingually.

In one embodiment of the invention, the human subject is administered an initial dose of 150 mg and a dose of 100 mg is administered to the human subject every 6 hours for about 1 day. In another embodiment, the human subject is administered an initial dose of 150 mg and a dose of 100 mg is administered to the human subject every 6 hours for about 2 days. In yet another embodiment, the human subject is administered an initial dose of 150 mg and a dose of 100 mg is administered to the human subject every 6 hours for about 5 days. In further embodiment, the human subject is administered an initial dose of 150 mg and a dose of 100 mg is administered to the human subject every 8 hours for about 1 day. In certain embodiment, the human subject is administered an initial dose of 150 mg and a dose of 100 mg is administered to the human subject every 8 hours for about 2 days. In another embodiment, the human subject is administered an initial dose of 150 mg and a dose of 100 mg is administered to the human subject every 8 hours for about 5 days. In yet another embodiment, the human subject is administered an initial dose of 150 mg and a dose of 100 mg is administered to the human subject every 12 hours for about 1 day. In another embodiment, the human subject is administered an initial dose of 150 mg and a dose of 100 mg is administered to the human subject every 12 hours for about 2 days. In further embodiment, the human subject is administered an initial dose of 150 mg and a dose of 100 mg is administered to the human subject every 12 hours for about 5 days. In yet another embodiment, the human subject is administered an initial dose of 150 mg and a dose of 150 mg is administered to the human subject every 6 hours for about 1 day. In another embodiment, the human subject is administered an initial dose of 150 mg and a dose of 150 mg is administered to the human subject every 6 hours for about 2 days. In yet another embodiment, the human subject is administered an initial dose of 150 mg and a dose of 150 mg is administered to the human subject every 6 hours for about 5 days. In another embodiment, the human subject is administered an initial dose of 150 mg and a dose of 150 mg is administered to the human subject every 8 hours for about 1 day. In certain embodiment, the human subject is administered an initial dose of 150 mg and a dose of 150 mg is administered to the human subject every 8 hours for about 2 days. In yet another embodiment, the human subject is administered an initial dose of 150 mg and a dose of 150 mg is administered to the human subject every 8 hours for about 5 days. In one embodiment, the human subject is administered an initial dose of 150 mg and a dose of 150 mg is administered to the human subject every 12 hours for about 1 day. In further embodiment, the human subject is administered an initial dose of 150 mg and a dose of 150 mg is administered to the human subject every 12 hours for about 2 days. In yet another embodiment, the human subject is administered an initial dose of 150 mg and a dose of 150 mg is administered to the human subject every 12 hours for about 5 days. In another embodiment, the human subject is administered an initial dose of 150 mg and a close of 200 mg is administered to the human subject every 6 hours for about 1 day. In one embodiment, the human subject is administered an initial dose of 150 mg and a close of 200 mg is administered to the human subject every 6 hours for about 2 days. In another embodiment, the human subject is administered an initial dose of 150 mg and a dose of 200 mg is administered to the human subject every 6 hours for about 5 days. In further embodiment, wherein the human subject is administered an initial dose of 150 mg and a dose of 200 mg is administered to the human subject every 8 hours for about 1 day. In yet another embodiment, the human subject is administered an initial dose of 150 mg and a dose of 200 mg is administered to the human subject every 8 hours for about 2 days. In one embodiment, the human subject is administered an initial dose of 150 mg and a dose of 200 mg is administered to the human subject every 8 hours for about 5 days. In another embodiment, the human subject is administered an initial dose of 150 mg and a dose of 200 mg is administered to the human subject every 12 hours for about 1 day. In further embodiment, the human subject is administered an initial dose of 150 mg and a dose of 200 mg is administered to the human subject every 12 hours for about 2 days. In another embodiment, the human subject is administered an initial dose of 150 mg and a dose of 200 mg is administered to the human subject every 12 hours for about 5 days. In certain embodiment, the human subject is administered an initial dose of 200 mg and a dose of 100 mg is administered to the human subject every 6 hours for about 1 day. In yet another embodiment, the human subject is administered an initial dose of 200 mg and a dose of 100 mg is administered to the human subject every 6 hours for about 2 days. In another embodiment, the human subject is administered an initial dose of 200 mg and a dose of 100 mg is administered to the human subject every 6 hours for about 5 days. In one embodiment, the human subject is administered an initial dose of 200 mg and a dose of 100 mg is administered to the human subject every 8 hours for about 1 day. In further embodiment, the human subject is administered an initial dose of 200 mg and a dose of 100 mg is administered to the human subject every 8 hours for about 2 days. In yet another embodiment, the human subject is administered an initial dose of 200 mg and a dose of 100 mg is administered to the human subject every 8 hours for about 5 days. In another embodiment, the human subject is administered an initial dose of 200 mg and a dose of 100 mg is administered to the human subject every 12 hours for about 1 day. In one embodiment, the human subject is administered an initial dose of 200 mg and a dose of 100 mg is administered to the human subject every 12 hours for about 2 days. In another embodiment, the human subject is administered an initial dose of 200 mg and a dose of 100 mg is administered to the human subject every 12 hours for about 5 days. In further embodiment, the human subject is administered an initial dose of 200 mg and a dose of 150 mg is administered to the human subject every 6 hours for about 1 day. In another embodiment of the invention, the human subject is administered an initial dose of 200 mg and a dose of 150 mg is administered to the human subject every 6 hours for about 2 days. In yet another embodiment, the human subject is administered an initial dose of 200 mg and a dose of 150 mg is administered to the human subject every 6 hours for about 5 days. In another embodiment, the human subject is administered an initial dose of 200 mg and a dose of 150 mg is administered to the human subject every 8 hours for about 1 day. In one embodiment, the human subject is administered an initial dose of 200 mg and a dose of 150 mg is administered to the human subject every 8 hours for about 2 days. In yet another embodiment, the human subject is administered an initial dose of 200 mg and a dose of 150 mg is administered to the human subject every 8 hours for about 5 days. In another embodiment, the human subject is administered an initial dose of 200 mg and a dose of 150 mg is administered to the human subject every 12 hours for about 1 day. In another embodiment, the human subject is administered an initial dose of 200 mg and a dose of 150 mg is administered to the human subject every 12 hours for about 2 days. In an embodiment of the invention, the human subject is administered an initial dose of 200 mg and a dose of 150 mg is administered to the human subject every 12 hours for about 5 days. In further embodiment, the human subject is administered an initial dose of 200 mg and a dose of 200 mg is administered to the human subject every 6 hours for about 1 day. In yet another embodiment, the human subject is administered an initial dose of 200 mg and a dose of 200 mg is administered to the human subject every 6 hours for about 2 days. In another embodiment, the human subject is administered an initial dose of 200 mg and a dose of 200 mg is administered to the human subject every 6 hours for about 5 days. In an embodiment of the invention, the human subject is administered an initial dose of 200 mg and a dose of 200 mg is administered to the human subject every 8 hours for about 1 day. In further embodiment, the human subject is administered an initial dose of 200 mg and a dose of 200 mg is administered to the human subject every 8 hours for about 2 days. In yet another embodiment, the human subject is administered an initial dose of 200 mg and a dose of 200 mg is administered to the human subject every 8 hours for about 5 days. In another embodiment, the human subject is administered an initial dose of 200 mg and a dose of 200 mg is administered to the human subject every 12 hours for about 1 day. In an embodiment of the invention, the human subject is administered an initial dose of 200 mg and a dose of 200 mg is administered to the human subject every 12 hours for about 2 days. In one embodiment, the human subject is administered an initial dose of 200 mg and a dose of 200 mg is administered to the human subject every 12 hours for about 5 days. In another embodiment, the human subject is administered a single or a divided dose of about 25 to about 300 mg of the compound or the pharmaceutical composition, for about between about 5 days to about 10 days. In yet another embodiment, the human subject is administered a divided dose of about 25 to about 300 mg of the compound, or the pharmaceutical composition, for about between about 5 days to about 10 days.

The compounds of the present invention can be administered in a single or a divided dose. In one embodiment, the human subject is administered a divided dose of about 25 to about 300 mg of a compound of Formula (I), or a pharmaceutical composition comprising a compound of Formula (I), for about between about 1 day to about 10 days. In another embodiment, the human subject is administered a single dose of about 25 to about 300 mg of a compound of Formula (I), or a pharmaceutical composition comprising a compound of Formula (I), for about between about 1 day to about 10 days.

Compounds of Formula (I) and Formula (II) inhibit the replication of a variety of laboratory and clinical dengue strains of DENV1-4, with submicromolar EC50 values. As used herein, "EC50" refers to the concentration of an anti-viral that produces 50% of the maximal possible anti-viral effect. In one embodiment, the method of the invention is used to treat an infection caused by at least one dengue virus selected from DENV1, DENV2, DENV3, and DENV4.

The method of the present invention is used to treat a dengue viral infection in a subject who has tested positive for a dengue virus. Known methods for diagnosis of dengue viral infection can be used including, but not limited to, an NS1 strip assay or a quantitative PCR assay. The selected method should be rapid enough for a diagnosis within from about onset of fever to about 72 hours of fever onset to optimize the therapeutic regimen of the various embodiments of the invention.

In one embodiment, the human subject tests positive for a dengue infection in a NS1 strip assay. In another embodiment, the human subject tests positive for a dengue infection in a quantitative PCR assay.

The compounds of the present invention can be administered intravenously, orally, rectally or sublingually. Intravenous, oral, rectal and sublingual dosing can be in a single or divided dose. Intravenous dosing can also be a slow infusion over a period of time and the slow infusions can be constant or intermittent.

The compounds of the invention can be administered several times a day or as needed to maintain a steady Cmin serum concentration of between about 0.05 and about 2.0 microgram/mL. A suitable interval between the two administrations includes any time period which maintains a therapeutically effective plasma level of a compound of Formula (I). Such an interval can be, for example, about 12 hours. In one embodiment, the human subject is administered a compound of Formula (I) or a compound of Formula (II) twice a day. Dosing at intervals is intended to cover subsequent dosing, either as a single or a divided dose, routinely during the course of therapy. For example, dosing can be about every 6 to about 12 hours during the course of treatment, but it is intended to cover the possibility that a dose may have been missed during at least one interval. In another embodiment, the human subject is administered a compound of Formula (I) or a compound of Formula (II) three times a day. In yet another embodiment, the human subject is administered a compound of Formula (I) or a compound of Formula (II) four times a day.

As such, a first dose can be administered at 6 am on Day 1 and a second dose can be administered at 6 pm on Day 1 for a total of two doses in a 24 hour period or day. Further, a first dose can be administered at 12 am on Day 1, a second dose can be administered at 6 am on Day 1, a third dose can be administered at 12 pm on Day 1, and a fourth dose can be administered at 6 pm on Day 1 for a total of four doses in a 24 hour period or day. In one embodiment, the therapeutically effective plasma level is the level at which the Cmin concentration of a compound of Formula (I) is achieved.

The invention also relates to a method of treating a dengue virus infection by achieving a steady state Cmin serum or plasma concentration of between about 0.05 and about 2.0 microgram/mL of castanospermine in an adult or child human subject. As used herein, "Cmin" refers to the minimum concentration that a drug achieves after the drug has been administered and prior to the administration of a second or additional dose. Steady state Cmin is achieved when the overall intake of a drug Cmin concentration is fairly in dynamic equilibrium with its elimination. In some embodiments, Cmin concentration of castanospermine is determined at one or more points following treatment with techniques known in the art.

In one embodiment, the steady state Cmin serum or plasma concentration achieved in an adult or child subject is between about 0.08 and about 0.5 microgram/mL of castanospermine. In another embodiment, the steady state Cmin serum or plasma concentration achieved in an adult or child subject is between about 0.05 and about 0.08 microgram/mL of castanospermine. In yet another embodiment, the steady state Cmin serum or plasma concentration achieved in an adult or child subject is between about 0.08 and about 0.11 microgram/mL of castanospermine. In a further embodiment, the steady state Cmin serum or plasma concentration achieved in an adult or child subject is between about 0.11 and about 0.3 microgram/mL of castanospermine. In another embodiment, the steady state Cmin serum or plasma concentration achieved in an adult or child subject is between about 0.3 and about 0.75 microgram/mL of castanospermine. In further embodiment, the steady state Cmin serum or plasma concentration achieved in an adult or child subject is between about 0.75 and about 1.0 microgram/mL of castanospermine. In yet another embodiment, the steady state Cmin serum or plasma concentration achieved in an adult or child subject is between about 1.0 and about 2.0 microgram/mL of castanospermine. In another embodiment, the steady state Cmin serum or plasma concentration achieved in an adult or child subject is between about 1.0 and about 1.5 microgram/mL of castanospermine. In further embodiment, the steady state Cmin serum or plasma concentration achieved in an adult or child subject is between about 1.5 and about 2.0 microgram/mL of castanospermine. In yet another embodiment, the steady state Cmin scrum or plasma concentration achieved in an adult or child subject is between about 1.25 and about 1.75 microgram/mL of castanospermine.

The invention further relates to a method of treating a dengue virus infection by achieving an average steady state Cmin serum or plasma concentration of between about 0.05 and about 2.0 microgram/mL of castanosperine in a plurality of human subjects after the administration of the compounds of the invention. The average steady state Cmin of the plurality of human subjects is calculated as an average of steady state Cmin serum or plasma concentrations from each of the plurality of human subjects. In certain embodiments of the invention, an average steady state Cmin serum or plasma concentration of between about 0.05 and about 2.0 microgram/mL of castanospermine in the plurality of human subjects is attained after treatment.

In one embodiment, the average steady state Cmin serum or plasma concentration achieved in the plurality of human subjects is between about 0.08 and about 0.5 microgram/mL of castanospermine. In another embodiment, the average steady state Cmin serum or plasma concentration achieved in the plurality of human subjects is between about 0.05 and about 0.08 microgram/mL of castanospermine. In yet another embodiment, the average steady state Cmin serum or plasma concentration achieved in the plurality of human subjects is between about 0.08 and about 0.11 microgram/mL of castanospermine. In a further embodiment, the average steady state Cmin serum or plasma concentration achieved in the plurality of human subjects is between about 0.11 and about 0.3 microgram/mL of castanospermine. In another embodiment, the average steady state Cmin serum or plasma concentration achieved in the plurality of human subjects is between about 0.3 and about 0.75 microgram/mL of castanospermine. In further embodiment, the average steady state Cmin serum or plasma concentration achieved in the plurality of human subjects is between about 0.75 and about 1.0 microgram/mL of castanospermine. In yet another embodiment, the average steady state Cmin serum or plasma concentration achieved in the plurality of human subjects is between about 1.0 and about 2.0 microgram/mL of castanospermine. In another embodiment, the average steady state Cmin serum or plasma concentration achieved in the plurality of human subjects is between about 1.0 and about 1.5 microgram/mL of castanospermine. In further embodiment, the average steady state Cmin serum or plasma concentration achieved in the plurality of human subjects is between about 1.5 and about 2.0 microgram/mL of castanospermine. In yet another embodiment, the average steady state Cmin serum or plasma concentration achieved in the plurality of human subjects is between about 1.25 and about 1.75 microgram/mL of castanospermine.

In another aspect, methods of the present invention can treat a secondary dengue infection or an “antibody enhanced” (ADE) dengue infection. A “secondary” infection refers to a DENV infection in a patient who was previously infected with DENV. An “antibody enhanced” infection refers to a DENV infection made more severe due to a prior infection with one of the four DENV serotypes. Ninety percent (90%) of severe and potentially fatal dengue diseases, such as dengue hemorrhagic fever (DHF) or dengue shock syndrome (DSS) are caused by a secondary dengue infection. In secondary dengue infection, prior infection causes generation of an antibody that takes on a pathogenic role. Upon reinfection with DENV, the antibody response triggers a systemic inflammatory reaction resulting in vascular leakage. In one embodiment, the dengue viral infection is a secondary dengue infection.

In another aspect of the invention, viral load reduction of a treated human subject is at least 50% greater than untreated or placebo-treated human subjects. As used herein, the term “viral load” refers to the amount of virus in the blood stream of a human subject. The viral load is measured before administration of the first dose and then at various time intervals after administration. The dose amounts can be adjusted to increase the viral load reduction or if no viral reduction is observed at a specific dose it can be adjusted to promote viral reduction.

In one embodiment, the virological log reduction in human subjects treated with a compound of Formula (I) is at least about 50% greater than untreated or placebo-treated groups. In another embodiment, the virological log reduction in human subjects treated with a compound of Formula (I) is between about 60 to 70% greater than untreated or placebo-treated groups. In another embodiment, the virological log reduction in human subjects treated with a compound of Formula (I) is between about 70 to 80% greater than untreated or placebo-treated groups. In yet another embodiment, the virological log reduction in human subjects treated with a compound of Formula (I) is between about 80 to 90% greater than untreated or placebo-treated groups.

EXAMPLES

Example 1: Cell-Based Flaviviral Immunodetection Assay (CFI)

BHK21 cells were seeded at 1.3×104 in 96-well plate and incubated overnight at 37° C. in 5% $CO_2$ incubator. Confluent monolayer of BHK21 cells were infected with DENV2 (TSV01 strain) at an MOT (multiplicity of infection) 0.3 in the presence of various concentrations of test compounds and incubated for 1 hour at 37° C. in 5% $CO_2$ incubator. Infected cells were incubated with test compounds for another 48 hours at 37° C. in 5% $CO_2$. Cells were fixed with methanol and mouse monoclonal antibody 4G2 was used to detect DENV E protein, which was quantified using a secondary anti-mouse antibody conjugated with horseradish peroxidase (HRP). Absorbance was read at 450 nm and dose-response curve was plotted accordingly. The 50% effective concentration (EC50), that is, the concentration of the test compound that decreased the level of viral E protein production by 50%, was calculated by nonlinear regression analysis.

Celgosivir inhibits virus production in a concentration-dependent manner with an EC50 0.22 μM for DENV2 (FIG. 1), The EC50 values for the other three serotypes are also in the sub-micromolar range (0.31 to 0.65 μM). Castanospermine (CAST) has an EC50 of ~21 μM against DENV2, which may be attributed to its lower uptake into cells compared with celgosivir.

The results are shown in Table 3.

TABLE 3

EC50 values of celgosivir hydrochloride on DENV 1-4 infection in the CFI assay.

| Dengue Serotype | CFI (EC50) | Compound |
|---|---|---|
| DENV1 | 0.65 ± 0.16 μM | Celgosivir |
| DENV2 | 0.22 ± 0.01 μM | Celgosivir |
| DENV3 | 0.68 ± 0.02 μM | Celgosivir |
| DENV4 | 0.31 ± 0.12 μM | Celgosivir |
| DENV2 | ~21 μM | Castanospermine |

Example 2: Fluorescence Microscopy

Figure 2:
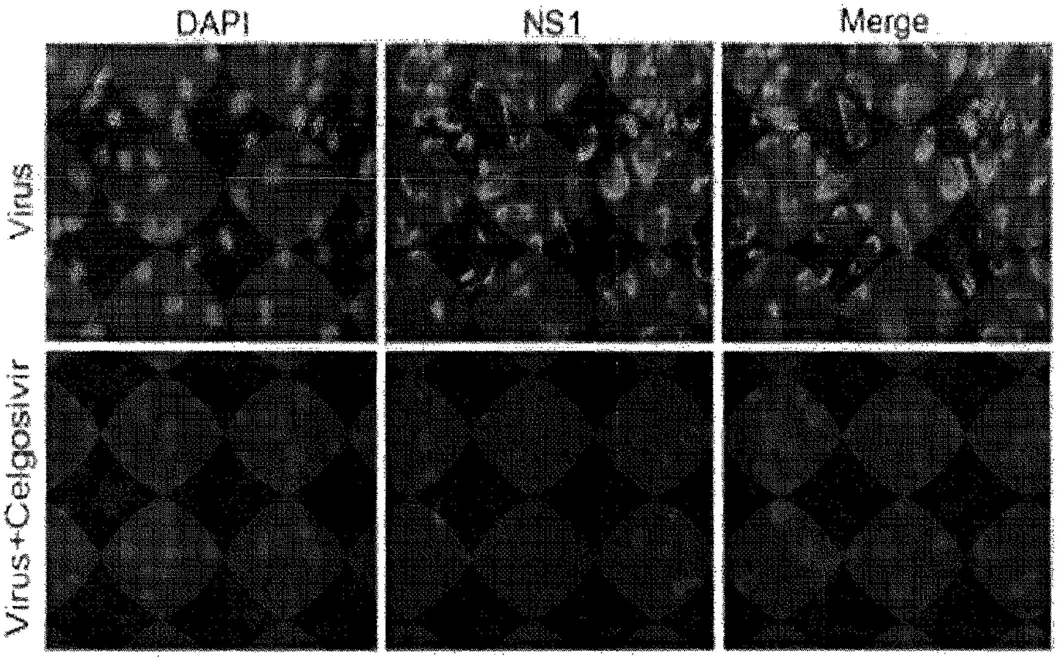
FIG. 2 shows immunofluorescence microscopy of untreated and celgosivir (20 μM) treated DENV2 infected BHK21. Nuclei are stained with blue fluorescent DAPI. Virus replication was detected using monoclonal anti-NS1 antibody (green fluorescence). The top row shows that untreated, infected cells have abundant NS1 in the cytoplasm while the bottom row shows that infected cells treated with celgosivir have very low levels of NS1. Low levels of NS1 indicate suppression of viral replication.

BHK21 cells were infected with DENV2 and treated with 20 μM celgosivir or saline. After 24 hr incubation, cells were stained with nuclear stain diamidino-2-phenylindole (DAPI) or with a MAb against NS1 in conjunction with a secondary antibody conjugated with Alexa-488 (green), then examined by fluorescent microscopy for the presence of NS1, a marker for viral replication. Viral-infected cells show abundant NS1 in the cytoplasm, whereas those treated with celgosivir have almost complete suppression of viral replication (FIG. 2).

Other cellular microscopic studies, which used specific antibodies that are markers for the endoplasmic reticulum (ER) or Golgi (BiP/Grp78) and Gigantin, respectively, were conducted and demonstrated that nonglycosylated NS1 accumulates in the ER and does not transport through the trans-Golgi network in order for it to be processed for secretion.

Celgosivir treatment also results in upregulation of pro-survival host gene products such as EDEM and XBP1, while apoptotic markers such as CHOP are down-regulated during drug-induced unfolded protein response (data not shown). The pro-survival products enhance the clearance of mis-folded proteins by directing them to the proteosome for degradation.

Example 3: Replicon Assay

The DENV subgenomic replicon was derived from the DENV2 strain NGC and consists of a luciferase reporter and a puromycin resistance gene for stable transfection. (7) Only the nonstructural proteins NS1, NS2A, NS2B, NS3, NS4A, NS4B, and NS5 were represented in the replicon construct. Of the nonstructural proteins, only NS1 is known to be glycosylated.

Figure 3:
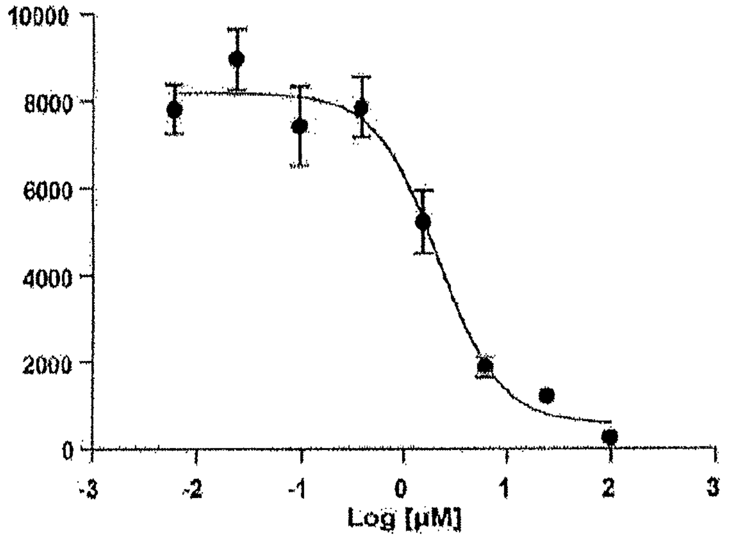
FIG. 3 shows the concentration response curve of celgosivir on DENV2 infection in the replicon assay ($EC_{50}$=2.2 μM).

The stably transfected A549 replicon cell line was plated into a 96-well plate in the presence of various concentrations of test compounds and incubated for 48 hour at 37° C. in 5% $CO_2$ incubator. The luciferase activity of the replicon treated with various concentrations of the test compound was measured using EnduRen (Promega) at a 1:1000 dilution followed by incubation for 2 hrs before the luminescence was read using a Tecan plate-reader. The data was plotted against the log transformation of the concentration of the compounds to obtain a dose-response curve to calculate the EC50 value. Celgosivir inhibited replicon production in a concentration-dependent manner, with an EC50 value of 2.2 (FIG. 3). This data shows inhibition of host alphaglucosidase activity by celgosivir targets both structural and non-structural dengue proteins and severely affects viral assembly and replication.

Example 4: ADE Infection of Human Monocytes

The activity of celgosivir in infected human monocytes, one of the primary circulating cell types infected by dengue virus, was examined. THP-1 cells were grown in RPMT-1640 maintenance medium containing 10% fetal calf serum and 1% Penicillin-streptomycin and cultured in 37° C. incubator supplemented with 5% $CO_2$. For ADE infection in THP-1 cells, virus (DENV2, MOT-10) was mixed with sub-neutralizing concentration of humanized 4G2 monoclonal antibody (0.05 μg/0.5 ml) and allowed to incubate on ice for 1 hr in the serum free medium, to allow immune complex formations. The immune complex was then added on to THP-1 ($1\times10^5$) cells per well in a 24 well plate and further incubated for 2 hours at 37° C. incubator. An excess unbound immune complex was then removed by spinning cells at 1000 rpm for 5 min and then cells were supplemented with complete growth maintenance medium. For drug testing in the ADE condition, cells were mock (untreated) or celgosivir-treated for 48 hours, and finally media supernatant was collected for plaque assay analysis.

Figure 4:
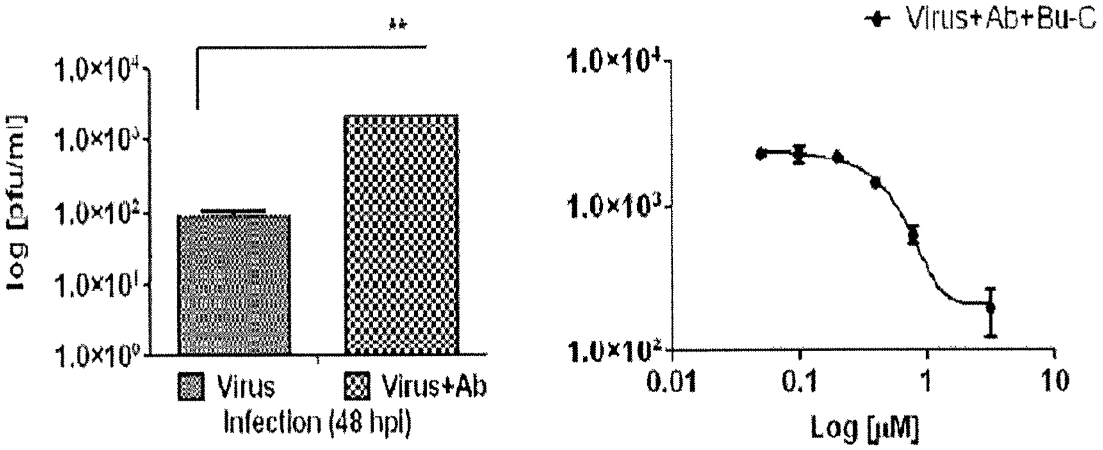
FIG. 4A shows the ADE effect—antibody against dengue E protein increases viremia in THP-1 human monocytes infected with dengue virus.
FIG. 4B shows the effect of celgosivir on DENV2 infected human monocytes pretreated with antibody to DENV E protein.

Addition of MAb against protein E results in a nearly 2 log increase in viremia (FIG. 4A). After addition of varying concentrations of celgosivir, viral replication was suppressed with an EC50 of 0.5 μM (FIG. 4B). Under the same conditions, Castanospermine was shown to suppress viral replication with an EC50 of 14 μM.

Example 5: Animal Models

Mouse Viremia Models

To develop an in vivo test system for anti-dengue drugs, immunocompetent Sv/129 mice deficient in type I and II interferon receptors (AG129), were injected with an unadapted, clinical strain of DENV2, resulting in a dose-dependent transient viremia lasting several days and peaking on day 3 after infection. (8) NS1 protein, proinflammatory cytokines, and neutralizing IgM and IgG antibodies were detected and also the mice had splenomegaly. (8) Selected compounds such as celgosivir significantly reduced viremia in a dose-dependent manner, even after delayed treatment, leading to a reduction of splenomegaly and proinflammatory cytokine levels. Thereby validating dengue this mouse model as a suitable system for testing anti-dengue drugs. Furthermore, they indicate that antiviral treatment during the acute phase of dengue fever can reduce the severity of the disease. (8) In the AG129 mouse model, celgosivir significantly reduced viremia by 88% and 55%, respectively, when given at the time of infection or after treatment was delayed by 24 hours.

To model ADE, mice were injected IP (intraperitoneal) with 15 mg of mouse monoclonal antibody against the (DENV) E protein (4G2 clone) one day prior to infection. (9) For treatment, celgosivir was injected IP once or twice daily for a total of 5 days. Mice were monitored every day till Day 12 post infection. The data were plotted as Kaplan-Meier curves using Prism 5.0 software.

In this lethal model of viremia, untreated mice had 0% survival by Day 5, whereas mice treated with 50 mg/kg celgosivir PO (oral) BID (twice a day), showed 100% survival even at Day 12 ($p=0.0001$). Even when treatment was delayed 24 and 48 hr, celgosivir was still able to confer protection, with 75% and 50% survival, respectively at Day 12. Dosing studies at 10, 25, and 50 mg/kg PO BID resulted in 12%, 62% and 100% survival respectively. Surprisingly when mice were treated once daily at 100 mg/kg PO, no mice survived past day 6 compared to 100% Survival at 50 mg/kg twice daily, indicating that the drug, when divided into two doses, is more effective than giving the same total dose once a day.

Example 6: Dosing and Schedule Effects

To evaluate the effect of dose and dose schedule, four drug regimens were studied in the ADE viremia model: 10, 25 and 50 mg/kg BID and 100 mg/kg QD (once daily). For the BID schedule, survival increased with increasing dose with survival rates of 13%, 63% and 100% for 10, 25, and 50 mg/kg BID. Survival rates were also sensitive to schedule −50 mg/kg BID dosing achieved complete protection, but the same total dose of 100 mg/kg given as a single daily dose failed to protect animals from death, with none surviving past Day 6. Even 25 mg/kg given BID was more effective than 100 mg/kg QD. Hence, dividing the dose was more effective than a larger daily dose.

Delayed Dosing

Figures 5A, 5B:
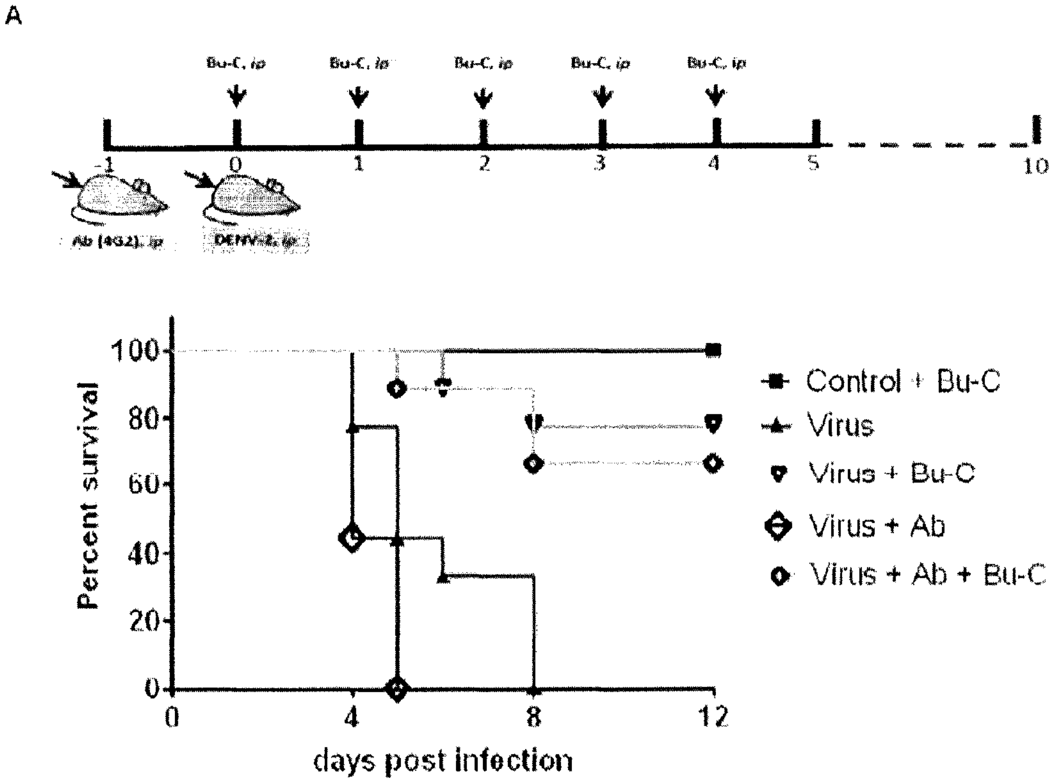
FIG. 5A shows a schematic of the dosing conducted in the DENV2 infected mice in a lethal ADE model of viremia.
FIG. 5B shows celgosivir improves survival of DENV2 infected mice in a lethal ADE model of viremia in a dose- and schedule-dependent manner. Survival at day 12 was 1/8 (13%) at 10 mg/kg twice daily (BID), 5/8 (63%) at 25 mg/kg BID, 7/7 (100%) at 50 mg/kg BID, and 0/8 (0%) at 100 mg/kg once daily (QD).

Even when treatment was delayed (FIG. 5A), celgosivir (50 mg/kg BID) exerted a protective effect. In this experiment, survival at Day 12 was 100%, 75%, and 50% when treatment was immediate, delayed 24 hr or delayed 48 hr after DENV2 infection, respectively, in the ADE model; by contrast, none (0%) of the sham-treated mice survived past day 5 (FIG. 5B). Viremia, as determined by plaque assay, in celgosivir-treated mice (50 mg/kg BID) was 8.3% of levels in sham-treated mice after only 1 day of dosing. By study day 3, viremia had increased in untreated mice by more than 7-fold. Celgosivir demonstrated significantly lower viremia in treated mice—levels were 17%, 26% and 69% of levels in sham-treated mice when treatment was immediate, delayed 24 hr, or delayed 48 hr, respectively. The results also demonstrate that lower viremia is associated with improved outcome.

Example 7: Pharmacokinetics Mouse Studies

Celgosivir is more rapidly and efficiently absorbed than castanospermine. In the mouse, single-dose celgosivir (25 mg/kg PC) demonstrated a 5-fold greater uptake into the plasma at 2 and 5 min post-dosing than a single dose of Castanospermine (16 mg/kg PO). At 5 min after administration of celgosivir, only castanospermine was detected in the plasma, confirming the rapid conversion of celgosivir into castanospermine.

Figures 6A, 6B:
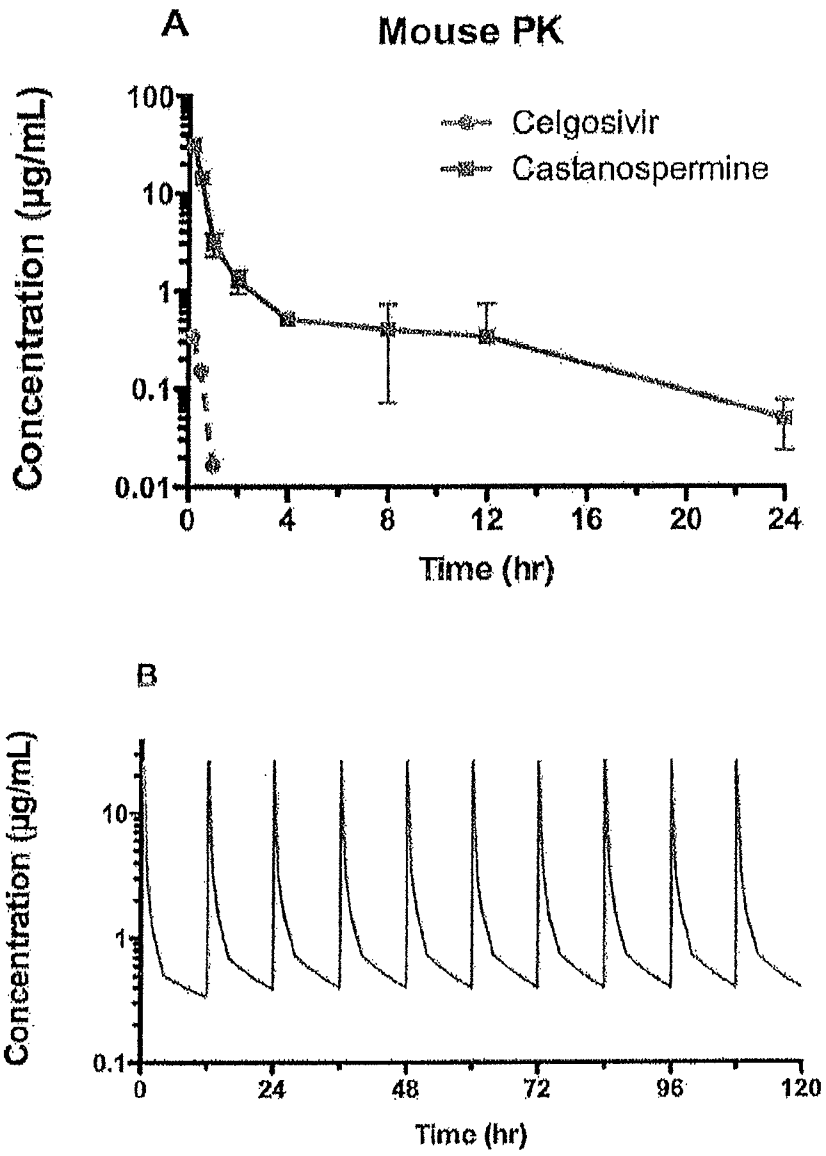
FIG. 6A shows a concentration profile of celgosivir and castanospermine after a single 50 mg/kg IP dose.
FIG. 6B shows a castanospermine profile calculated for 50 mg/kg BID dosing regimen.

The concentration profile of celgosivir and castanospermine in the mouse after a single IP dose of celgosivir at a dose of 50 mg/kg is illustrated in FIG. 6A. Serum concentrations were measured using a validated LC/MS/MS assay performed. Celgosivir was measurable in serum only up to 1 hr post-dosing. Conversion to castanospermine is rapid, and the maximal castanospermine concentration (Cmax) of 31.6 μg/mL occurs at the first sampling time of 10 min post-dosing. AUC was 22.8 μg·hr/ml. Apparent clearance (CL/F) was 2.2 L/h/kg, mean residence time was 3.5 hr, and the terminal half-life was 5.0 hr.

The castanospermine concentration profile after dosing at 50 mg/kg BID for 5 days was calculated by nonparametric superposition (FIG. 6B). This dosing regimen of celgosivir protected 100% of mice in the lethal ADE dengue infection model. Steady state Cmin and Cmax were 0.4 μg/mL and 26.4 μg/mL, respectively.

Rat studies have been published. The published data shows that following a single dose of celgosivir in healthy rats at 35 mg/kg PO, Cmax, Tmax and AUC values were 8.76±1.15 μg/ml, 0.44±0.01 brand 10.5 μg·hr/ml, respectively. (10) Oral bioavailability in the rat was 93%, oral clearance (CL/F) was 2.5 L/h/kg, and half-life was 2.7 hr. The anti-diarrhea agent loperamide had no effect on the PK in either normal rats or those with castor oil-induced diarrhea. (11)

In rats administered radiolabeled castanospermine, the majority of radioactivity was detected within urine after PO (oral) or IV dosing within 24 hr, and more than 92% was identified as castanospermine. (12)

In rats with portal vein catheters administered 400 mg/kg celgosivir PO, celgosivir concentrations in the portal vein were approximately 4.4 to 13.2-fold higher than those in peripheral circulation. The mean Cmax of celgosivir in the portal vein was 1.9 μg/ml compared with 105.6 μg/mL for castanospermine. AUC 0-60 min was 1.0 μg·hr/ml for celgosivir vs. 63.9 μg·hr/ml for castanospermine. (10) Hence the majority of celgosivir was converted to castanospermine prior to liver exposure, probably in the gastrointestinal tract.

The maximum tolerated dose) in humans was determined in studies conducted as part of HIV drug trials. The MTD was 400 mg per day for 184 days. (13)

Example 8: Effect of Diet on Gastrointestinal Effects of Glucosidase Inhibitors

Mice given a high dose of castanospermine (2 g/kg), when fed with sucrose- and starch containing diets develop severe diarrhea and high intestinal bacterial counts. (14) This is believed to be due to off-target inhibition of gastrointestinal α-amylase, sucrase, maltase and other enzymes involved in sucrose and glycogen breakdown. Celgosivir is a weaker inhibitor than castanospermine of the above-mentioned gastrointestinal enzymes. (10) When mice were fed a diet of proteins, vitamins and glucose and which did not contain sucrose or other complex sugars and carbohydrates, the UI toxicity of castanospermine was ameliorated.

Example 9: Safety Pharmacology

Human Safety Pharmacology

Previous studies have provided valuable information on the clinical pharmacology, pharmacokinetics, safety and tolerability of celgosivir in humans. These studies have included single and multiple dosing as well as QD dosing ranging from 10 to 600 mg for 2 to 12 weeks.

In humans, celgosivir has been shown to rapidly convert to castanospermine where only the latter was detected in plasma. The celgosivir was also shown to rapidly absorb with peak concentrations of castanospermine occurring between 0.3 and 1.3 hr. Cmax and AUC were also shown to increase in proportion to dose. The terminal half-life for celgosivir in humans was 18 hr, and oral clearance was 12 L/hr. (15)

Celgosivir is rapidly converted to castanospermine, which is excreted unchanged in the urine, with no other metabolites detected. Adverse events were largely gastrointestinal, namely flatulence and diarrhea, of mild to moderate intensity. Asymptomatic elevations in serum creatine kinase were also observed, which were reversed within 2 weeks after discontinuation of the drug. No serious adverse events have been reported.

Example 10: Treatment of a Dengue Infection in an Adult Subject with Celgosivir Hydrochloride

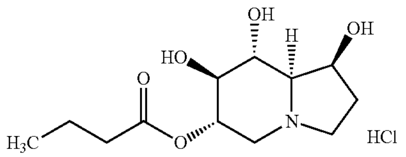 [SMILES: CCCC(=O)O[C@H]1CN2CC[C@H](O)[C@@H]2[C@@H](O)[C@@H]1O ; Cl]

A human subject was orally administered an initial loading dose of 400 mg of celgosivir followed by a maintenance dose of 200 mg every 12 hr for a total of nine (9) doses. Drug was taken by the human subject without food, i.e., 1 hr before consuming food or 2 hr afterwards. Subject was also placed on a special diet of protein, vitamins, and glucose containing minimal complex sugars or starches to minimize the likelihood of gastrointestinal side effects. During treatment, several serum and urine samples were obtained to analyze for drug levels.

On fifth day of treatment, after blood draws, administration of the last dose, safety assessments, determination of risk for DI-IF or DSS, and satisfactory clinical status, the human subject were discharged. Blood sampling and safety assessments were then made on Days 7, 10, and 15. Human subjects completed visual analog scales for joint and muscle pain (VASP), and were evaluated for safety and tolerability daily during treatment and at each subsequent visit. Virological log reduction (VLR) was examined from Day 2 to 4. Viral clearance, serum NS1 levels, leukocyte and platelet count, and hemoconcentration were also determined.

Example 11: Pharmacokinetic Model

Population pharmacokinetic (PK) analysis of castanospermine plasma concentration data after administration of celgosivir was performed using the non-linear mixed effects modelling software NONMEM (version 7.2.0). (16) Pharmacokinetic parameters were estimated using the first order conditional estimation method (FOCE) with eta-epsilon interaction. Due to limited data during the input phase, first-order absorption/formation of castanospermine was assumed. Between-subject variability was assumed to be log-normally distributed. Model development was guided by objective function value (OFV), precision of the parameter estimates, inspection of standard goodness of fit plots and scientific plausability. The emperical Bayes estimates from the final model were used to predict individual concentrations for a standard saturated sampling design (i.e., samples collected at 0, 0.25, 0.5, 1, 1.5, 2, 4, 6 and 12 hours post-dose) after the first dose (400 mg) and dose 9 (day 5; 200 mg). These data were then use to determine the non-compartmental PK analysis (NCA) parameters area under the concentration-time curve over the dosing interval ($AUC_{tau}$), maximum concentration ($C_{max}$), time of maximum concentration ($T_{max}$) and minimum concentration ($C_{min}$). The NCA parameter values were derived using the statistical analysis software R (version 3.0.1). (17) NCA parameters after dose 9 were only determined for subject who received this dose. The mean NCA PK parameter values used to estimate the model-dependent parameter values were taken from the results of a Phase I trial investigating celgosivir and castanospermine PK after multiple doses (10-450 mg/day for 14 days) of celgosivir in HIV-positive patients. (18, 19)

These data are reproduced in Table 4.

TABLE 4

NCA PK Parameter Values

| Dose (mg) | $AUC_{ss}$ (mg · h/L) | $C_{max, ss}$ (ng/mL) | $t_{max}$ (h) | $C_{min, ss}$ (ng/mL) | $t_{1/2}$ (h) |
|---|---|---|---|---|---|
| 10 | 1.00 | 0.2266 | 0.7 | 8 | 13 |
| 20 | 1.75 | 0.52 | 1 | 11 | 27 |
| 40 | 3.61 | 1.07 | 1 | 23 | 30 |
| 80 | 6.53 | 1.72 | 0.3 | 29 | 16 |
| 160 | 13.30 | 3.73 | 0.8 | 70 | 21 |
| 240 | 21.50 | 5.76 | 0.6 | 110 | 16 |
| 360 | 32.10 | 6.319 | 0.7 | 179 | 15 |
| 450 | 39.80 | 10.50 | NR | 191 | 14 |

Note:
The 80 and 450 mg dosing groups were excluded from the analysis conducted.
$AUC_{ss}$ is area under the concentration-time curve at steady-state, $C_{max, ss}$ is the maximum concentration at steady-state, $t_{max}$ is the time of maximum concentration, $C_{min}$ is the minimum concentration at steady-state, $t_{1/2}$ is the terminal elimination half-life. NR represents values that were not reported.

Figure 7:
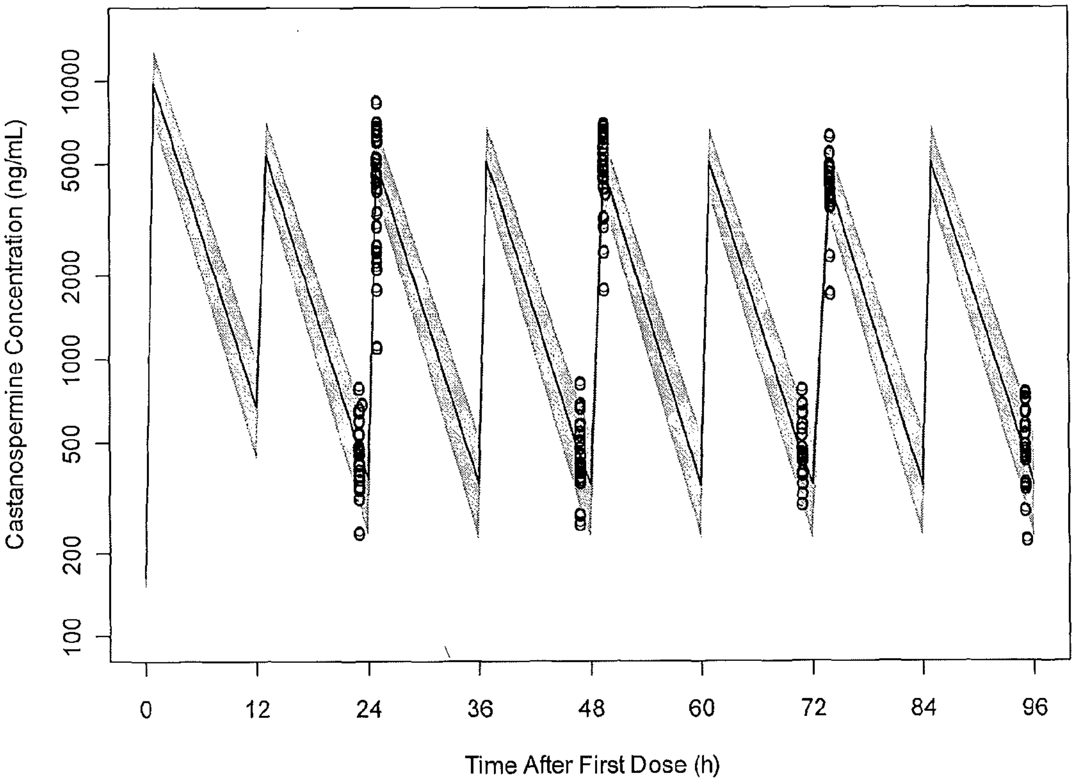
FIG. 7 shows the castanospermine concentration-time data over the treatment period. Circles represent observed concentrations. Shaded grey area represents the model predicted $10^{th}$ to $90^{th}$ prediction interval. Solid line represents the $50^{th}$ prediction interval.
Figures 8A, 8B, 8C:
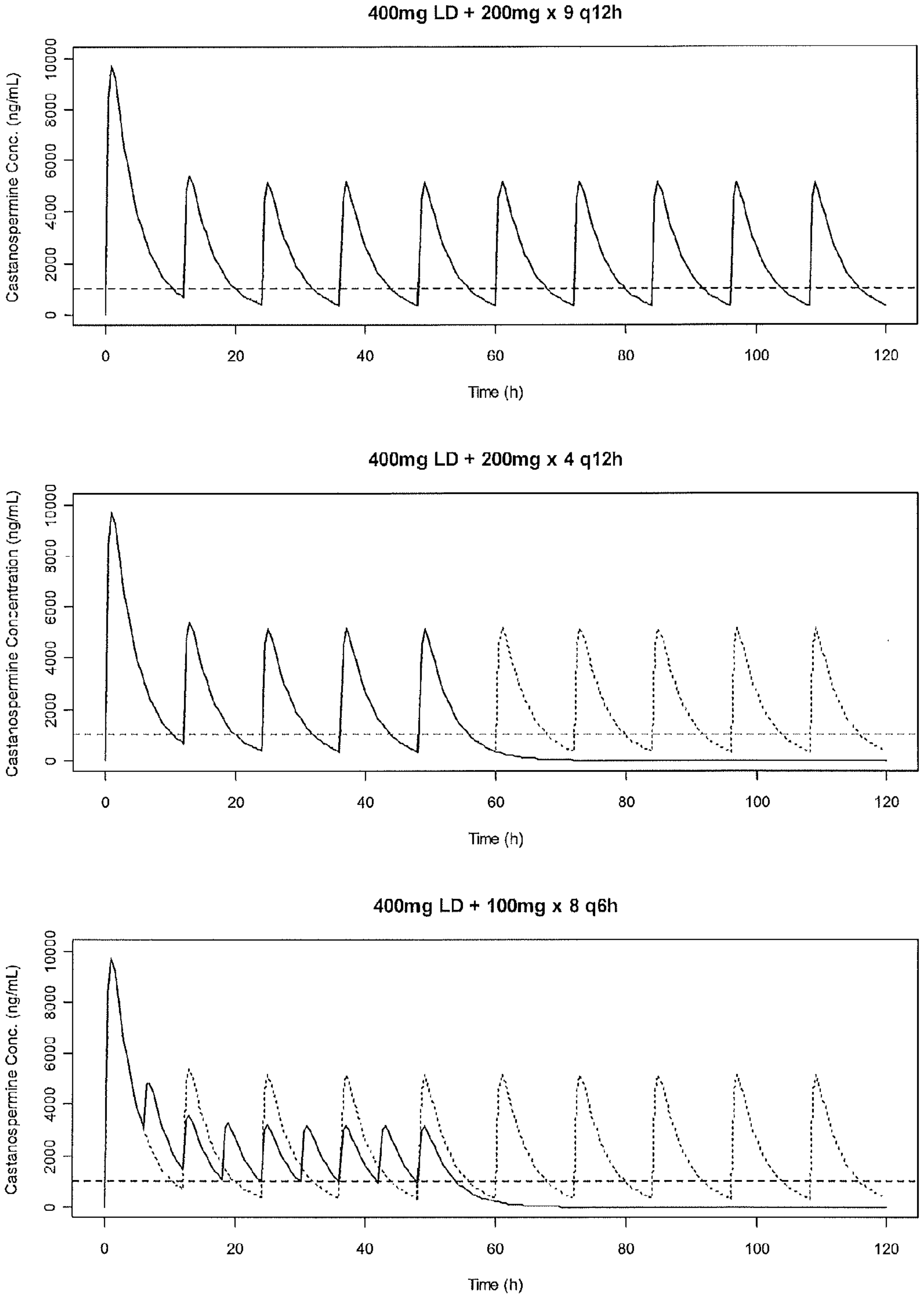
FIG. 8A shows a simulated population mean castanospermine exposure after a 400 mg loading dose of celgosivir followed by 9 subsequent doses of 200 mg of celgosivir given at 12 hour intervals. 8B shows a simulated population mean castanospermine exposure after a 400 mg loading dose of celgosivir followed by 4 subsequent doses of 200 mg of celgosivir given at 12 hour intervals. 8C shows a simulated population mean castanospermine exposure after a 400 mg loading dose of celgosivir followed by 8 subsequent doses of 100 mg of celgosivir given at 6 hour intervals. 8D shows a simulated population mean castanospermine exposure after a 400 mg loading dose of celgosivir followed by 6 subsequent doses of 133 mg of celgosivir given at 8 hour intervals. 8E shows a simulated population mean castanospermine exposure after a 300 mg loading dose of celgosivir followed by 3 subsequent doses of 300 mg of celgosivir given at 12 hour intervals. 8F shows a simulated population mean castanospermine exposure after a 200 mg loading dose of celgosivir followed by 5 subsequent doses of 200 mg of celgosivir given at 8 hour intervals. 8G shows a simulated population mean castanospermine exposure after a 150 mg loading dose of celgosivir followed by 7 subsequent doses of 150 mg of celgosivir given at 6 hour intervals. 8H shows a simulated population mean castanospermine exposure after a single dose of 600 mg. For FIGS. 8A-8H the solid line represents the simulated dosing regimen, the dotted line represents a dosing regimen of 400 mg initial dose followed by 200 mg every 12 hours for 9 doses (i.e. 5 days of treatment) and the dashed line represents target minimum trough concentration. LD is loading dose. q is 'every' and refers to the duration of time between doses.
Figures 8D, 8E, 8F:
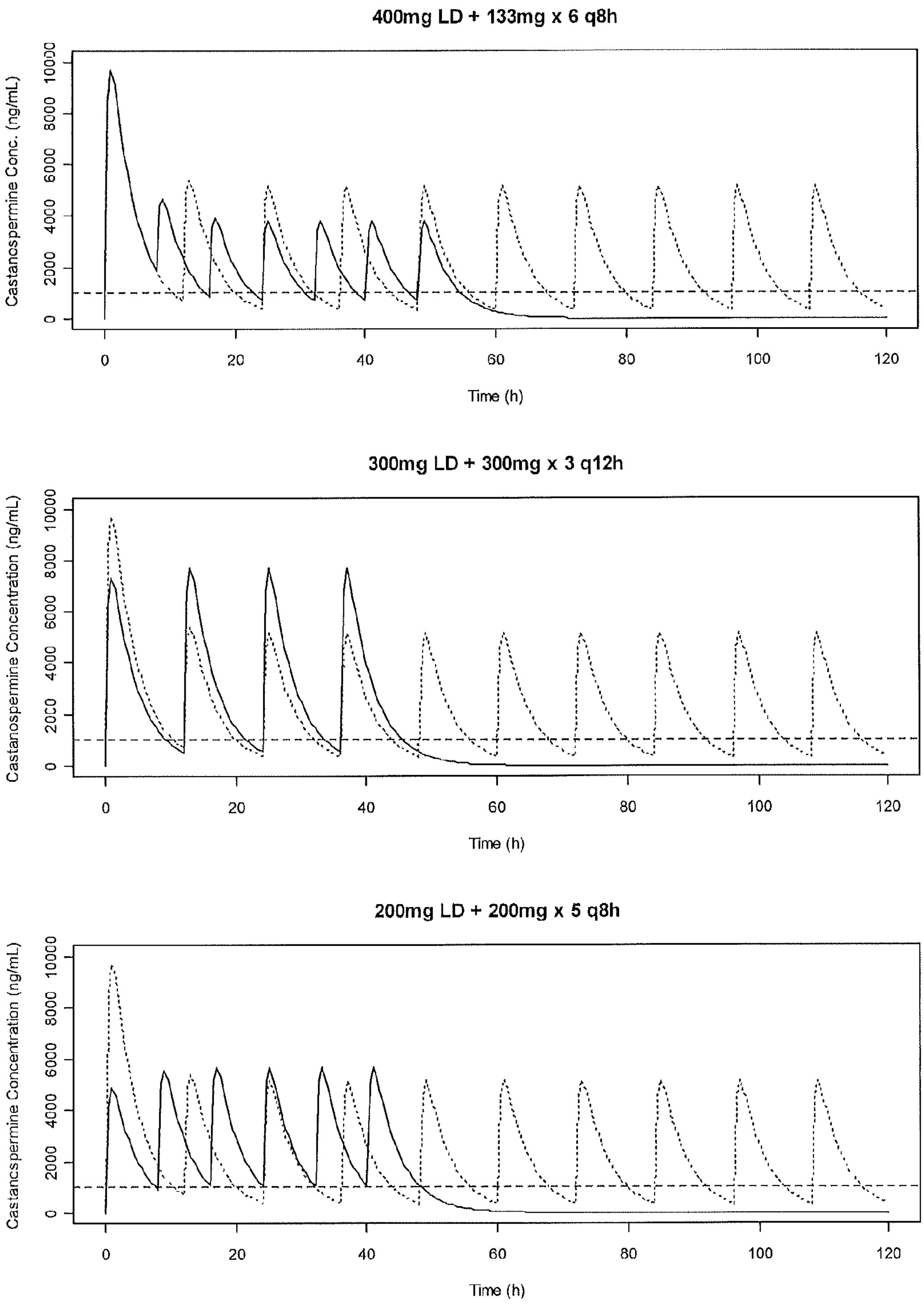
Figures 8G, 8H:
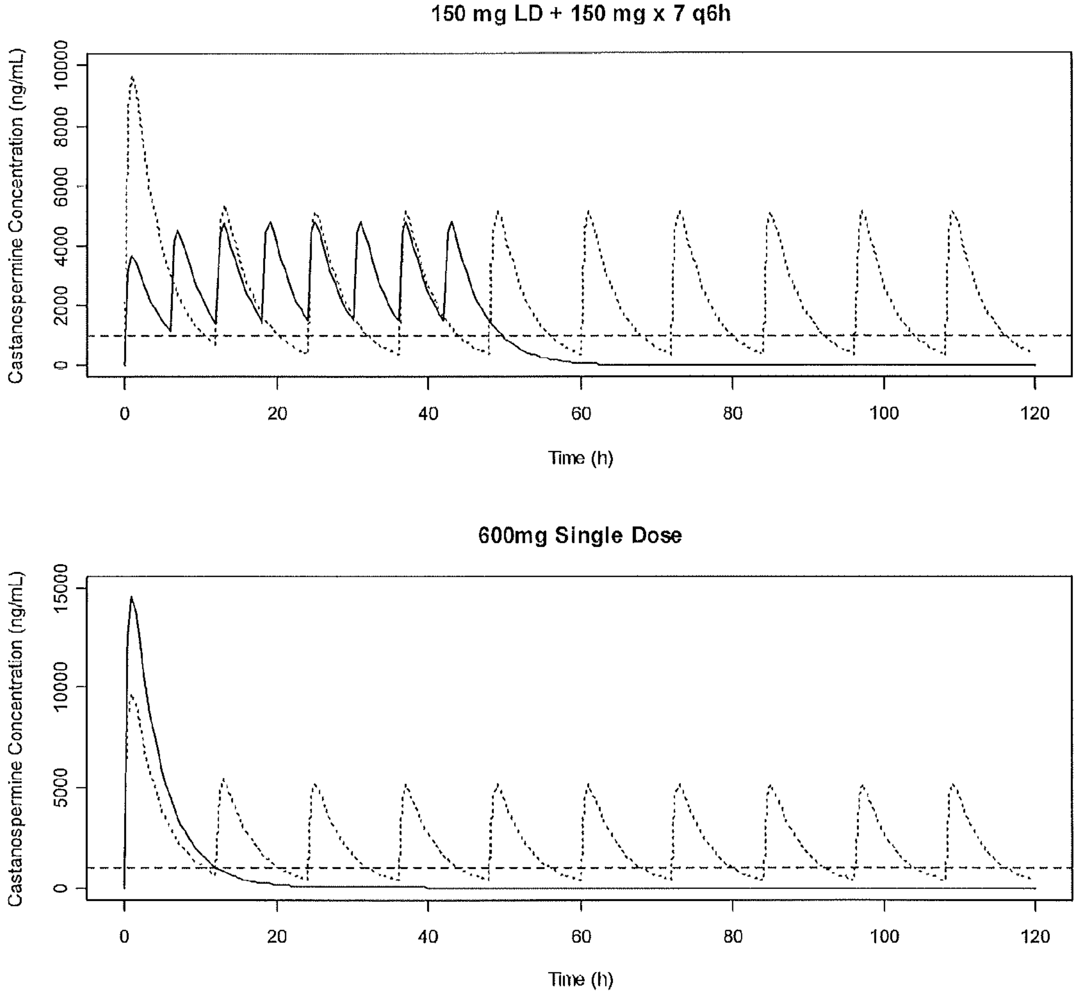

A sparse PK sampling design was employed with plasma samples collected at pre-dose and 23, 25, 47, 49.5, 71, 74 and 95 hours after first dose administration, (20) A total of 50 otherwise healthy patients who had dengue fever were enrolled and randomly assigned in a 1:1 ratio to receive either celgosivir or placebo. Active treatment participants received a 400 mg loading dose followed by 200 mg every 12 hours for 9 doses (i.e. 5 days of treatment). A total of 163 concentrations from 24 individuals were available for analysis. Pharmacokinetic data were best described by a 1-compartment model with first-order input and elimination. No time-dependent changes in PK were observed. A plot of measured concentrations overlayed with the $10^{th}$ to $90^{th}$ prediction interval from data simulated for 2000 individuals demonstrates the model adequately describes the data and is illustrated in FIG. 7. The predicted individual NCA parameter values after doses 1 and 9 are summarised in Table 5. No major accumulation was observed, with mean exposure (i.e. $C_{max}$ and $AUC_{tau}$) on day 5 (dose 9; 200 mg) less than that after first dose (400 mg). Variability in exposure between subjects was considered small to moderate.

TABLE 5

Predicted non-compartmental pharmacokinetic parameters after doses 1 and 9.

| Parameter | | Dose 1 (400 mg; 0-12 h) [n = 24] | Dose 9 (200 mg; 96-108 h) [n = 22] |
|---|---|---|---|
| $AUC_{tau}$ | Mean (SD) | 48691 (2980) | 25703 (1912) |
| (ng · h/mL) | Median (Range) | 48125 (42107, 54821) | 25384 (21727, 28977) |
| Cmax | Mean (SD) | 9703 (129) | 5127 (135) |
| (ng/mL) | Median (Range) | 9684 (9394, 9950) | 5105 (4844, 5422) |
| Tmax | Mean (SD) | 1 (na) | 1 (na) |
| (h) | Median (Range) | 1 (1, 1) | 1 (1, 1) |
| Cmin | Mean (SD) | 684 (153) | 357 (85) |
| (ng/mL) | Median (Range) | 647 (385, 1025) | 339 (198, 555) |

Plots of simulated population mean castanospermine concentration-time profiles after various celgosivir dosing regimens are presented in FIG. 8A-H. The regimen that best produced trough concentrations above 1000 ng/mL while reducing peak concentrations relative to the dosing protocol described above (400 mg loading dose followed by 200 mg every 12 hours for 9 doses) was administration of a 150 mg loading dose followed by 150 mg every 6 hours for 7 doses.

REFERENCES

1. WHO (2009). "Dengue and dengue hemorrhagic fever fact sheet 117." World Health Organization.
2. Fink J, Gu F and Vasudevan S G (2006). "Role of T cells, cytokines and antibody in dengue fever and dengue haemorrhagic fever." Rev Med Virol 16(4): 263-75.
3. Halstead S B (2007). "Dengue." Lancet 370(9599): 1644-52.
4. Remme J H, Bias E, Chitsulo L et al. (2002), "Strategic emphases for tropical diseases research: a TDR perspective." Trends Parasitol 18(10): 421-6.
5. Courageot M P, Frenkiel M P, Dos Santos C D et al. (2000). "Alpha-glucosidase inhibitors reduce dengue virus production by affecting the initial steps of virion morphogenesis in the endoplasmic reticulum." Journal of Virology 74(1): 564-72.
6. Rathore A P S, Paradkar P N, Watanabe S et al. (2011). "Celgosivir treatment misfolds dengue virus NS1 protein, induces cellular pro-survival genes and protects against lethal challenge mouse model." ANTIVIRAL RESEARCH 92(3): 453-60.

7. Ng C Y, Gu F, Phong W Y et al. (2007). "Construction and characterization of a stable subgenomic dengue virus type 2 replicon system for antiviral compound and siRNA testing." Antiviral Res 76(3): 222-31.

8. Schul W, Liu W, Xu H-Y et al. (2007). "A dengue fever viremia model in mice shows reduction in viral replication and suppression of the inflammatory response after treatment with antiviral drugs." J INFECT DIS 195(5): 665-74.

9. Zellweger R M, Prestwood T R and Shresta S (2010). "Enhanced infection of liver sinusoidal endothelial cells in a mouse model of antibody-induced severe dengue disease." Cell Host Microbe 7(2): 128-39.

10. Durantel D (2009). "Celgosivir, an alpha-glucosidase I inhibitor for the potential treatment of HCV infection." Curr Opin Investig Drugs 10(8): 860-70.

11. Erik D, Rubinchik E, Pasetka H et al. (2005). "Pharmacokinetics of celgosivir (MX-3253), a novel a-glucosidase I inhibitor in loperamide-treated and diarrhea-induced rats." Antiviral Research 65: 1-1.

12. Sorbera L A, Castaner J and Garcia-Capdevila L (2005). "Celgosivir." Drugs of the Future 30(6): 545-552.

13. Roth H, McPherson M, Hamedani P et al. (1996). "Phase I tolerance and pharmacokinetics of a new castanospermine derivative, MDL 28,574A." Int Conf AIDS Abstracts: 1-1.

14. Saul R, Ghidoni J J, Molyneux R J et al. (1985). "Castanospermine inhibits alpha-glucosidase activities and alters glycogen distribution in animals." Proc Natl Acad Sci USA 82(1): 93-7.

15. Stoltz M and Arumugham T (1996). "Single and multiple dose proportionality study of MDL 28,574. Study No. NDPR0005." Hoeschst Marion Roussel (Report No. K-96-0262-D): 579p.

16. Beal S L, Sheiner L B, Boeckmann A J, Bauer R J. "NONMEM Users Guides." ICON Development Solutions, Ellicott City, Md., USA. 1989-2011.

17. R Core Team. R: "A Language and Environment for Statistical Computing." R Foundation for Statistical Computing, Vienna, Austria, 2013.

18. L. Sorbera, J. Castaner and L. Garcia-Capdevila, "Celgosivir," *Drugs of the Future*, vol. 30, no. 6, pp. 545-552, 2005.

19. C. Sung, S. Vasudevan, J. Low and E. Ooi, "Celgosivir Investigator's Brochure," Duke-NUS Graduate Medical School, Singapore, 2012.

20. Duke-NUS Graduate Medical School Program for Emerging Infectious Diseases, "Clinical Protocol EID-DF-01 Celgosivir Proof of Concept Trial for Treatment of Acute Dengue Fever (CELADEN)," 2012.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a dengue virus (DENV) infection in a human subject, comprising:

a) administering to the human subject an initial dose of about 100 to about 600 mg of a compound of Formula (II), or a pharmaceutical composition comprising a compound of Formula (II), within from about onset of fever to about 72 hours of fever onset due to dengue infection; and b) administering to the human subject a dose of about 25 to about 300 mg of a compound of Formula (II), or a pharmaceutical composition comprising a compound of Formula (II), at intervals of from about 6 to about 12 hours until there is an improvement in the infection or between from about 1 day to about 10 days, Formula (II), having the following structure, (II)

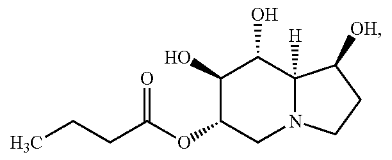

or a pharmaceutically acceptable salt thereof.

2. A method of treating a secondary dengue infection in a human subject, comprising:

a) administering to the human subject an initial dose of about 100 to about 600 mg of a compound of Formula (II), or a pharmaceutical composition comprising a compound of Formula (II), within from about onset of fever to about 72 hours of fever onset due to dengue infection; and b) administering to the human subject a dose of about 25 to about 300 mg of a compound of Formula (II), or a pharmaceutical composition comprising a compound of Formula (II), at intervals of from about 6 to about 12 hours until there is an improvement in the infection or between from about 1 day to about 10 days, Formula (II) having the following structure, (II)

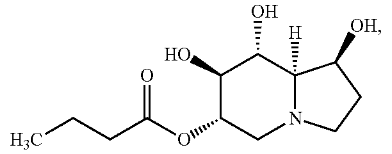

or a pharmaceutically acceptable salt thereof.

3. A method of treating a dengue virus (DENV) infection in a human subject, comprising:

a) administering orally to the human subject an initial dose of about 100 to about 600 mg of a compound of Formula (II), or a pharmaceutical composition comprising a compound of Formula (II), within from about onset of fever to about 72 hours of fever onset due to dengue infection; and b) administering orally to the human subject a dose of about 25 to about 300 mg of a compound of Formula (II), or a pharmaceutical composition comprising a compound of Formula (II), at intervals of from about 6 to about 12 hours until there is an improvement in the infection or between from about 1 day to about 10 days, Formula (II) having the following structure, (II)

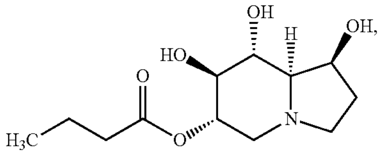

or a pharmaceutically acceptable salt thereof.

4. The method of claim 1 or claim 2, wherein the human subject is an adult or a child.

5. The method of claim 1, wherein the compound of Formula (II) is converted to castanospermine after administration to a human subject.

6. The method of claim 1, wherein a steady state Cmin serum or plasma concentration of between about 0.05 and about 2.0 microgram/mL of castanospermine in an adult or child human subject is attained after treatment.

7. The method of claim 1, wherein a steady state Cmin serum or plasma concentration of between about 1.0 and about 2.0 microgram/mL of castanospermine in an adult or child human subject is attained after treatment.

8. The method of claim 1, wherein a steady state Cmin serum or plasma concentration of between about 1.0 and about 1.5 microgram/mL of castanospermine in an adult or child human subject is attained after treatment.

9. The method of claim 1, wherein a steady state Cmin serum or plasma concentration of between about 1.5 and about 2.0 microgram/mL of castanospermine in an adult or child human subject is attained after treatment.

10. The method of claim 1, wherein a steady state Cmin serum or plasma concentration of between about 1.25 and about 1.75 microgram/mL of castanospermine in an adult or child human subject is attained after treatment.

11. The method of claim 1, wherein dengue viral infection comprises at least one dengue virus selected from DENV1, DENV2, DENV3 and DENV4.

12. The method of claim 1, wherein the dengue viral infection is secondary dengue infection.

13. The method of claim 1, wherein the human subject to be treated is positive prior to treatment for a dengue infection using a NS1 strip assay or quantitative PCR.

14. The method of claim 1, wherein the virological log reduction in treated human subjects is at least 50% greater than untreated or placebo-treated groups.

15. The method of claim 1, wherein administering the compound, or the pharmaceutical composition, achieves a steady state Cmin serum or plasma concentration of between about 0.05 and about 2.0 microgram/mL of castanospermine.

16. The method of claim 1, wherein administering the compound, or the pharmaceutical composition, achieves a steady state Cmin serum or plasma concentration of between about 1.0 and about 2.0 microgram/mL of castanospermine.

17. The method of claim 1, wherein administering the compound, or the pharmaceutical composition, achieves a steady state Cm in serum or plasma concentration of between about 1.0 and about 1.5 microgram/mL of castanospermine.

18. The method of claim 1, wherein administering the compound, or the pharmaceutical composition, achieves a steady state Cmin serum or plasma concentration of between about 1.5 and about 2.0 microgram/mL of castanospermine.

19. The method of claim 1, wherein administering the compound, or the pharmaceutical composition, achieves a steady state Cmin serum or plasma concentration of between about 1.25 and about 1.75 microgram/mL of castanospermine.

20. The method of claim 1, wherein the compound, or the pharmaceutical composition, is administered intravenously, orally, rectally, or sublingually.

21. The method of claim 1, wherein the human subject is administered an initial dose of 150 mg and a dose of 100 mg is thereafter administered to the human subject every 6 hours, 8 hours, or 12 hours for about 1 day, about 2 days, or about 5 days.

22. The method of claim 1, wherein the human subject is administered an initial dose of 150 mg and a dose of 150 mg is thereafter administered to the human subject every 6 hours for about 1 day, about 2 days, or about 5 days.

23. The method of claim 1, wherein the human subject is administered an initial dose of 150 mg and a dose of 150 mg is thereafter administered to the human subject every 8 hours for about 1 day, about 2 days, or about 5 days.

24. The method of claim 1, wherein the human subject is administered an initial dose of 150 mg and a dose of 150 mg is thereafter administered to the human subject every 12 hours for about 1 day, about 2 days, or about 5 days.

25. The method of claim 1, wherein the human subject is administered an initial dose of 150 mg and a dose of 200 mg is thereafter administered to the human subject every 6 hours, 8 hours, or 12 hours for about 1 day, about 2 days, or about 5 days.

26. The method of claim 1, wherein the human subject is administered an initial dose of 200 mg and a dose of 100 mg is thereafter administered to the human subject every 6 hours, 8 hours, or 12 hours for about 1 day, about 2 days, or about 5 days.

27. The method of claim 1, wherein the human subject is administered an initial dose of 200 mg and a dose of 150 mg is thereafter administered to the human subject every 6 hours, 8 hours, or 12 hours for about 1 day, about 2 days, or about 5 days.

28. The method of claim 1, wherein the human subject is administered an initial dose of 200 mg and a dose of 200 mg is thereafter administered to the human subject every 6 hours, 8 hours, or 12 hours for about 1 day, about 2 days, or about 5 days.

29. The method of claim 1, wherein the human subject is administered a single or a divided dose of about 25 to about 300 mg of the compound or the pharmaceutical composition, for about between about 5 days to about 10 days.

30. The method of claim 29, wherein the human subject is administered a divided dose of about 25 to about 300 mg of the compound, or the pharmaceutical composition, for about between about 5 days to about 10 days.

31. A method of treating a dengue virus (DENV) infection in a plurality of human subjects, comprising:

a) administering to each of the plurality of human subjects an initial dose of about 100 to about 600 mg of a compound of Formula (II), or a pharmaceutical composition comprising a compound of Formula (II), within from about onset of fever to about 72 hours of fever onset due to dengue infection; and b) administering to each of the plurality of human subjects a dose of about 25 to about 300 mg of a compound of Formula (II), or a pharmaceutical composition comprising a compound of Formula (II), at intervals of from about 6 to about 12 hours until there is an improvement in the infection or between from about 1 day to about 10 days, Formula (II) having the following structure, (II)

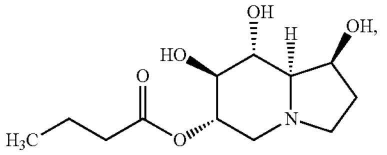

or a pharmaceutically acceptable salt thereof.

32. A method of treating a secondary dengue infection in a plurality of human subjects, comprising:

a) administering to each of the plurality of human subjects an initial dose of about 100 to about 600 mg of a compound of Formula (II), or a pharmaceutical composition comprising a compound of Formula (II), within from about onset of fever to about 72 hours of fever onset due to dengue infection; and b) administering to each of the plurality of human subjects a dose of about 25 to about 300 mg of a compound of Formula (II), or a pharmaceutical composition comprising a compound of Formula (II), at intervals of from about 6 to about 12 hours until there is an improvement in the infection or between from about 1 day to about 10 days, Formula (II) having the following structure, (II)

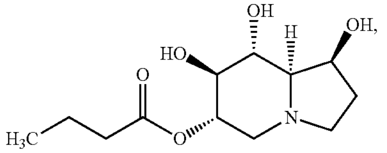

or a pharmaceutically acceptable salt thereof.

33. A method of treating a dengue virus (DENV) infection in a plurality of human subjects, comprising:

a) administering orally to each of the plurality of human subjects an initial dose of about 100 to about 600 mg of a compound of Formula (II), or a pharmaceutical composition comprising a compound of Formula (II), within from about onset of fever to about 72 hours of fever onset due to dengue infection; and b) administering orally to each of the plurality of human subjects a dose of about 25 to about 300 mg of a compound of Formula (II), or a pharmaceutical composition comprising a compound of Formula (II), at intervals of from about 6 to about 12 hours until there is an improvement in the infection or between from about 1 day to about 10 days, Formula (II) having the following structure, (II)

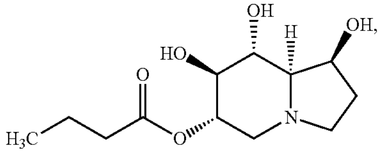

or a pharmaceutically acceptable salt thereof.

34. The method of claim 31 or claim 32, wherein the plurality of human subjects includes adults and/or children.

35. The method of claim 31, wherein the compound of Formula (II) is converted to castanospermine after administration to each of the plurality of human subjects.

36. The method of claim 31, wherein an average steady state Cmin serum or plasma concentration of between about 0.05 and about 2.0 microgram/mL of castanospermine in the plurality of human subjects is attained after treatment.

37. The method of claim 31, wherein an average steady state Cmin serum or plasma concentration of between about 1.0 and about 2.0 microgram/mL of castanospermine in the plurality of human subjects is attained after treatment.

38. The method of claim 31, wherein an average steady state Cmin serum or plasma concentration of between about 1.0 and about 1.5 microgram/mL of castanospermine in the plurality of human subjects is attained after treatment.

39. The method of claim 31, wherein an average steady state Cmin serum or plasma concentration of between about 1.5 and about 2.0 microgram/mL of castanospermine in the plurality of human subjects is attained after treatment.

40. The method of claim 31, wherein an average steady state Cmin serum or plasma concentration of between about 1.25 and about 1.75 microgram/mL of castanospermine in the plurality of human subjects is attained after treatment.

41. The method of claim 31, wherein dengue viral infection comprises at least one dengue virus selected from DENV1, DENV2, DENV3 and DENV4.

42. The method of claim 31, wherein the dengue viral infection is secondary dengue infection.

43. The method of claim 31, wherein each of the plurality of human subjects to be treated is positive prior to treatment for a dengue infection using a NS1 strip assay or quantitative PCR.

44. The method of claim 31, wherein the virological log reduction in treated plurality of human subjects is at least 50% greater than untreated or placebo-treated groups.

45. The method of claim 31, wherein administering the compound, or the pharmaceutical composition, achieves an average steady state Cmin serum or plasma concentration in the plurality of human subjects of between about 0.05 and about 2.0 microgram/mL of castanospermine.

46. The method of claim 31, wherein administering the compound, or the pharmaceutical composition, achieves an average steady state Cmin serum or plasma concentration in the plurality of human subjects of between about 1.0 and about 2.0 microgram/mL of castanospermine.

47. The method of claim 31, wherein administering the compound, or the pharmaceutical composition, achieves an average steady state Cmin serum or plasma concentration in the plurality of human subjects of between about 1.0 and about 1.5 microgram/mL of castanospermine.

48. The method of claim 31, wherein administering the compound, or the pharmaceutical composition, achieves an average steady state Cmin serum or plasma concentration in the plurality of human subjects of between about 1.5 and about 2.0 microgram/mL of castanospermine.

49. The method of claim 31, wherein administering the compound, or the pharmaceutical composition, achieves an average steady state Cmin serum or plasma concentration in the plurality of human subjects of between about 1.25 and about 1.5 microgram/mL of castanospermine.

50. The method of claim 31, wherein the compound, or the pharmaceutical composition, is administered intravenously, orally, rectally, or sublingually.

51. The method of claim 31, wherein each of the plurality of human subjects is administered an initial dose of 150 mg and a dose of 100 mg is thereafter administered to each of the plurality of human subjects every 6 hours, 8 hours, or 12 hours for about 1 day, about 2 days, or about 5 days.

52. The method of claim 31, wherein each of the plurality of human subjects is administered an initial dose of 150 mg and a dose of 150 mg is thereafter administered to each of the plurality of human subjects every 6 hours for about 1 day, about 2 days, or about 5 days.

53. The method of claim 31, wherein each of the plurality of human subjects is administered an initial dose of 150 mg and a dose of 150 mg is thereafter administered to each of the plurality of human subjects every 8 hours for about 1 day, about 2 days, or about 5 days.

54. The method of claim 31, wherein each of the plurality of human subjects is administered an initial dose of 150 mg and a dose of 150 mg is thereafter administered to each of the plurality of human subjects every 12 hours for about 1 day, about 2 days, or about 5 days.

55. The method of claim 31, wherein each of the plurality of human subjects is administered an initial dose of 150 mg and a dose of 200 mg is thereafter administered to each of the plurality of human subjects every 6 hours, 8 hours, or 12 hours for about 1 day, about 2 days, or about 5 days.

56. The method of claim 31, wherein each of the plurality of human subjects is administered an initial dose of 200 mg and a dose of 100 mg is thereafter administered to each of the plurality of human subjects every 6 hours, 8 hours, or 12 hours for about 1 day, about 2 days, or about 5 days.

57. The method of claim 31, wherein each of the plurality of human subjects is administered an initial dose of 200 mg and a dose of 150 mg is thereafter administered to each of the plurality of human subjects every 6 hours, 8 hours, or 12 hours for about 1 day, about 2 days, or about 5 days.

58. The method of claim 31, wherein each of the plurality of human subjects is administered an initial dose of 200 mg and a dose of 200 mg is thereafter administered to each of the plurality of human subjects every 6 hours, 8 hours, or 12 hours for about 1 day, about 2 days, or about 5 days.

59. The method of claim 31, wherein each of the plurality of human subjects is administered a single or a divided dose of about 25 to about 300 mg of the compound or the pharmaceutical composition, for about between about 5 days to about 10 days.

60. The method of claim 59, wherein each of the plurality of human subjects is administered a divided dose of about 25 to about 300 mg of the compound, or the pharmaceutical composition, for about between about 5 days to about 10 days.

61. The method of claim 1, wherein said doses of step b) are administered at least 3 times per day.

62. The method of claim 2, wherein said doses of step b) are administered at least 3 times per day.

63. The method of claim 3, wherein said doses of step b) are administered at least 3 times per day.

64. The method of claim 31, wherein said doses of step b) are administered at least 3 times per day.

65. The method of claim 32, wherein said doses of step b) are administered at least 3 times per day.

66. The method of claim 33, wherein said doses of step b) are administered at least 3 times per day.

* * * * *